(12) United States Patent
Woudenberg et al.

(10) Patent No.: US 8,247,219 B2
(45) Date of Patent: Aug. 21, 2012

(54) DEVICE AND METHOD FOR MULTIPLE ANALYTE DETECTION

(75) Inventors: Timothy Woudenberg, Moss Beach, CA (US); Michael Albin, Antioch, CA (US); Reid B. Kowallis, Burlingame, CA (US); Yefim Raysberg, Fremont, CA (US); Robert P. Ragusa, Los Altos, CA (US); Emily S. Winn-Deen, Foster City, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 318 days.

(21) Appl. No.: 11/811,504

(22) Filed: Jun. 11, 2007

(65) Prior Publication Data

US 2008/0102462 A1    May 1, 2008

Related U.S. Application Data

(63) Continuation of application No. 11/029,968, filed on Jan. 5, 2005, now Pat. No. 7,244,622, which is a continuation of application No. 09/628,076, filed on Jul. 28, 2000, now Pat. No. 7,235,406, which is a continuation of application No. 08/831,983, filed on Apr. 2, 1997, now Pat. No. 6,126,899.

(60) Provisional application No. 60/014,712, filed on Apr. 3, 1996.

(51) Int. Cl.
*C12M 1/34* (2006.01)
*C12M 3/00* (2006.01)

(52) U.S. Cl. ............... 435/287.2; 436/501; 436/518; 436/164; 436/807; 422/50; 422/82.05; 422/82.08; 422/68.1; 435/288.4; 435/288.5; 435/288.7

(58) Field of Classification Search ............... 435/287.2, 435/288.4, 288.5, 288.7; 436/501, 518, 164, 436/807; 422/50, 82.05, 82.08, 68.1
See application file for complete search history.

(56) References Cited

U.S. PATENT DOCUMENTS

| | | |
|---|---|---|
| 3,088,847 A | 5/1963 | Pines |
| 3,963,355 A | 6/1976 | Aldridge, Jr. et al. |
| 4,038,151 A | 7/1977 | Fadler et al. |
| 4,101,356 A | 7/1978 | Savelkouls |
| 4,305,720 A | 12/1981 | Bernstein |
| 4,349,510 A | 9/1982 | Kolehmainen et al. |

(Continued)

FOREIGN PATENT DOCUMENTS

EP    0 131 934 A2    1/1985

(Continued)

OTHER PUBLICATIONS

Albin, M. et al., Micromachining and Microgenetics: *What are They and Where do They Work Together*, Meeting Abstract (Jun. 1996).

(Continued)

*Primary Examiner* — Melanie J Yu

(57) ABSTRACT

The invention is directed to a method and device for simultaneously testing a sample for the presence, absence, and/or amounts of one or more of a plurality of selected analytes. The invention includes, in one aspect, a device for detecting or quantitating a plurality of different analytes in a liquid sample. Each chamber may include an analyte-specific reagent effective to react with a selected analyte that may be present in the sample, and detection means for detecting the signal. Also disclosed are methods utilizing the device.

16 Claims, 4 Drawing Sheets

U.S. PATENT DOCUMENTS

| | | | |
|---|---|---|---|
| 4,908,187 A | 3/1990 | Holmquist et al. | |
| 4,975,175 A | 12/1990 | Karube et al. | |
| 5,034,506 A | 7/1991 | Summerton et al. | |
| 5,164,055 A | 11/1992 | Dubrow | |
| 5,200,051 A | 4/1993 | Cozzette et al. | |
| 5,212,050 A | 5/1993 | Mier et al. | |
| 5,229,297 A | 7/1993 | Schnipelsky et al. | |
| 5,245,410 A | 9/1993 | Villuendas et al. | |
| 5,252,294 A | 10/1993 | Kroy et al. | |
| 5,270,183 A | 12/1993 | Corbett et al. | |
| 5,290,418 A | 3/1994 | Menchen et al. | |
| 5,296,375 A | 3/1994 | Kricka et al. | |
| 5,304,487 A | 4/1994 | Wilding et al. | |
| 5,391,250 A | 2/1995 | Cheney, II et al. | |
| 5,427,946 A | 6/1995 | Kricka et al. | |
| 5,443,890 A | 8/1995 | Ohman | |
| 5,455,175 A | 10/1995 | Wittwer et al. | |
| 5,498,392 A | 3/1996 | Wilding et al. | |
| 5,500,071 A | 3/1996 | Kaltenbach et al. | |
| 5,545,531 A | 8/1996 | Rava et al. | |
| 5,585,242 A | 12/1996 | Bouma et al. | |
| 5,589,350 A * | 12/1996 | Bochner | 435/29 |
| 5,612,473 A | 3/1997 | Wu et al. | |
| 5,616,478 A | 4/1997 | Chetverin et al. | |
| 5,620,845 A | 4/1997 | Gould et al. | |
| 5,629,158 A * | 5/1997 | Uhlen | 435/6.14 |
| 5,639,612 A | 6/1997 | Mitsuhashi et al. | |
| 5,645,801 A | 7/1997 | Bouma et al. | |
| 5,656,506 A | 8/1997 | Kawaguchi et al. | |
| 5,658,508 A | 8/1997 | Yukawa et al. | |
| 5,658,802 A | 8/1997 | Hayes et al. | |
| 5,807,522 A | 9/1998 | Brown et al. | |
| 5,843,767 A | 12/1998 | Beattie | |
| 5,846,727 A | 12/1998 | Soper et al. | |
| 5,856,174 A | 1/1999 | Lipshutz et al. | |
| 5,858,804 A | 1/1999 | Zanzucchi et al. | |
| 5,925,517 A | 7/1999 | Tyagi et al. | |
| 5,948,673 A | 9/1999 | Cottingham | |
| 5,951,952 A | 9/1999 | O'Bear et al. | |
| 5,958,698 A | 9/1999 | Chetverin et al. | |
| 5,989,638 A | 11/1999 | Nielsen | |
| 6,015,902 A | 1/2000 | Bieniarz et al. | |
| 6,124,138 A | 9/2000 | Woudenberg et al. | |
| 6,126,899 A | 10/2000 | Woudenberg et al. | |
| 6,334,980 B1 | 1/2002 | Hayes et al. | |
| 6,355,429 B1 | 3/2002 | Nygren et al. | |
| 6,627,159 B1 | 9/2003 | Bedingham et al. | |
| 6,660,517 B1 | 12/2003 | Wilding et al. | |
| 6,825,047 B1 | 11/2004 | Woudenberg et al. | |
| 6,830,936 B2 | 12/2004 | Anderson et al. | |
| 6,953,676 B1 | 10/2005 | Wilding et al. | |
| 7,211,443 B2 | 5/2007 | Woudenberg | |
| 7,235,406 B1 | 6/2007 | Woudenberg et al. | |
| 7,244,622 B2 | 7/2007 | Woudenberg et al. | |
| 7,381,569 B2 | 6/2008 | Woudenberg et al. | |
| 7,381,570 B2 | 6/2008 | Woudenberg et al. | |
| 7,381,571 B2 | 6/2008 | Woudenberg et al. | |
| 7,687,280 B2 | 3/2010 | Woudenberg et al. | |
| 2002/0192664 A1 | 12/2002 | Nygren et al. | |
| 2003/0152994 A1 | 8/2003 | Woudenberg et al. | |
| 2003/0198984 A1* | 10/2003 | Yang et al. | 435/6 |
| 2005/0019902 A1 | 1/2005 | Mathies et al. | |
| 2005/0282156 A1 | 12/2005 | Rava et al. | |
| 2006/0128007 A1 | 6/2006 | Woudenberg et al. | |
| 2006/0188917 A1 | 8/2006 | Woudenberg et al. | |
| 2006/0204401 A1 | 9/2006 | Woudenberg et al. | |
| 2008/0102461 A1* | 5/2008 | Woudenberg et al. | 435/6 |
| 2008/0102462 A1 | 5/2008 | Woudenberg et al. | |
| 2008/0108074 A1 | 5/2008 | Drmanac | |

FOREIGN PATENT DOCUMENTS

| | | |
|---|---|---|
| EP | 0 233 053 A2 | 8/1987 |
| EP | 0 496 200 A2 | 7/1992 |
| EP | 0640828 B1 | 5/2000 |
| WO | WO 91/17823 | 11/1991 |
| WO | WO 91/19823 | 12/1991 |
| WO | 92/02638 A1 | 2/1992 |
| WO | WO 93/22053 | 11/1993 |
| WO | WO 93/22054 | 11/1993 |
| WO | WO 93/22055 | 11/1993 |
| WO | WO 93/22058 | 11/1993 |
| WO | WO 93/22421 | 11/1993 |
| WO | WO 94/11489 | 5/1994 |
| WO | WO 95/06508 | 3/1995 |
| WO | WO 95/06870 | 3/1995 |
| WO | WO 95/21382 | 8/1995 |
| WO | WO 96/03206 | 2/1996 |
| WO | WO 96/04547 | 2/1996 |

OTHER PUBLICATIONS

International Search Report from PCT Application No. PCT/US97/05458.
Jacobson et al., *Microchip Electrophoresis with Sample Stacking*, Electrophoresis, 16:481-486 (1995).
Northrup, M.A. et al., *DNA Amplification with a Microfabricated Reaction Chamber*, Transducers, 924-926 (1993).
Ramsey, J.M. et al., *Microfabricated Chemical Measurement Systems*, Nature Medicine, 1(10):1093-1096 (1995).
Wilding, P. et al., *PCR in a Silicon Microstructure*, Clin. Chem. 40(9):1815-1818 (1994).
Wittwer, C.T. et al., *Automated Polymerase Chain Reaction in Capillary Tubes with Hot Air*, Nucleic Acids Research 17(11):4353-4357 (1989).
Wittwer, C.T. et al, *Minimizing the Time Required for DNA Amplification by Efficient Heat Transfer to Small Samples*, Analytical Biochemistry 186:328-331 (1990).
Wittwer, C.T. et al., Rapid Cycle DNA Amplification: *Time and Temperature Optimization*, BioTechniques 10(1):7683 (1991).
Baileys and Scott, "Diagnostic Microbiology", 1990, pp. 144-147, 8th Edition.
U.S. Appl. No. 11/400,610 Office Action dated Sep. 24, 2007.
U.S. Appl. No. 11/400,610 Office Action dated Apr. 2, 2008.
U.S. Appl. No. 11/400,610 Restriction Requirement dated Sep. 23, 2008.
U.S. Appl. No. 11/400,610 Office Action dated Feb. 2, 2009.
U.S. Appl. No. 11/400,610 Office Action dated Sep. 24, 2009.
U.S. Appl. No. 11/400,610 Office Action dated Feb. 4, 2010.
U.S. Appl. No. 11/400,610 Office Action dated Jun. 29, 2010.
U.S. Appl. No. 11/400,610 Office Action dated Apr. 28, 2011.
U.S. Appl. No. 11/431,363 Restriction Requirement dated Aug. 24, 2007.
U.S. Appl. No. 11/431,363 Office Action dated Nov. 20, 2007.
U.S. Appl. No. 11/431,363 Office Action dated Apr. 15, 2008.
U.S. Appl. No. 11/431,363 Restriction Requirement dated Oct. 16, 2008.
U.S. Appl. No. 11/431,363 Office Action dated Jan. 21, 2009.
U.S. Appl. No. 11/431,363 Office Action dated Jul. 22, 2009.
U.S. Appl. No. 11/431,363 Office Action dated Dec. 7, 2010.
U.S. Appl. No. 11/651,317 Restriction Requirement dated Oct. 14, 2008.
U.S. Appl. No. 11/651,317 Office Action dated Aug. 17, 2009.
U.S. Appl. No. 11/651,317 Office Action dated Feb. 18, 2010.
U.S. Appl. No. 11/651,317 Office Action dated Sep. 1, 2010.
U.S. Appl. No. 11/651,317 Office Action dated Mar. 25, 2011.
U.S. Appl. No. 11/651,321 Office Action dated Aug. 14, 2009.
U.S. Appl. No. 11/651,321 Restriction Requirement dated Oct. 16, 2008.
U.S. Appl. No. 11/651,321 Office Action dated Jan. 26, 2009.
U.S. Appl. No. 11/651,321 Office Action dated Feb. 3, 2010.
U.S. Appl. No. 11/651,321 Office Action dated Jun. 30, 2010.
U.S. Appl. No. 11/651,321 Notice of Allowance dated May 11, 2011.
U.S. Appl. No. 11/811,476 Office Action dated Feb. 4, 2010.
U.S. Appl. No. 11/811,476 Office Action dated Nov. 9, 2010.
U.S. Appl. No. 11/811,476 Office Action dated May 16, 2011.
2,250,212 CA Office Action dated Dec. 31, 2001.
2,250,212 CA Office Action dated Jan. 9, 2004.
2,250,212 CA Office Action dated Jan. 17, 2006.
2,250,212 CA Office Action dated Feb. 16, 2007.
2,250,212 CA Office Action dated Apr. 16, 2008.
9-535575 JP Office Action dated Mar. 2, 2007.

9-535575 JP Office Action dated Oct. 6, 2010.
2008-229123 JP Office Action dated Jul. 24, 2009.
2008-229123 JP Office Action dated Nov. 30, 2010.
Ishiguro, et al, "Homogeneous Quantitative Assay of Hepatitis C Virus RNA by Polymerase Chain Reaction in the Presence of a Fluorescent Intercalater" *Analytical Biochemistry*, vol. 229, (1995), pp. 207-213.

Zhu, "High-Sensitivity Capillary Electrophoresis of Double-Stranded DNA Fragments Using Monomeric and Dimeric Fluorescent Intercalating Dyes" *Analytical Chemistry*, vol. 66, No. 13, (1994), pp. 1941-1948.

* cited by examiner

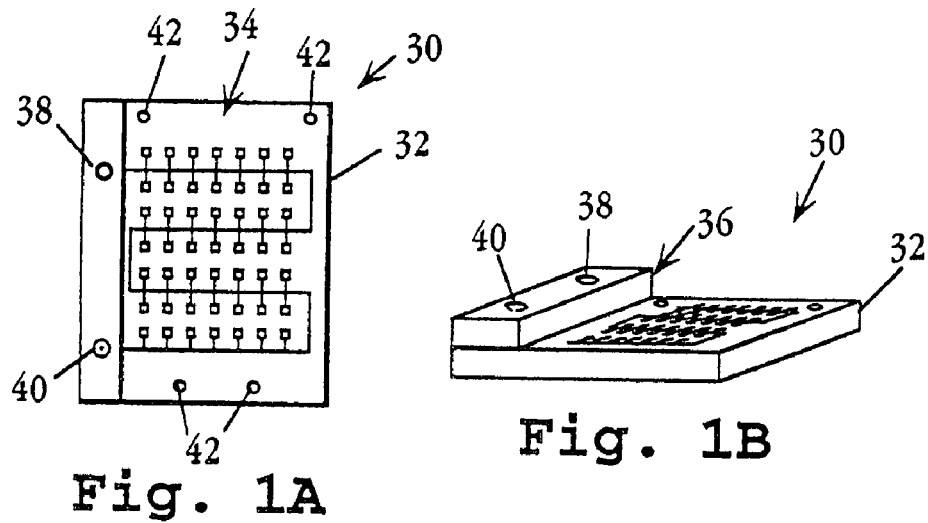
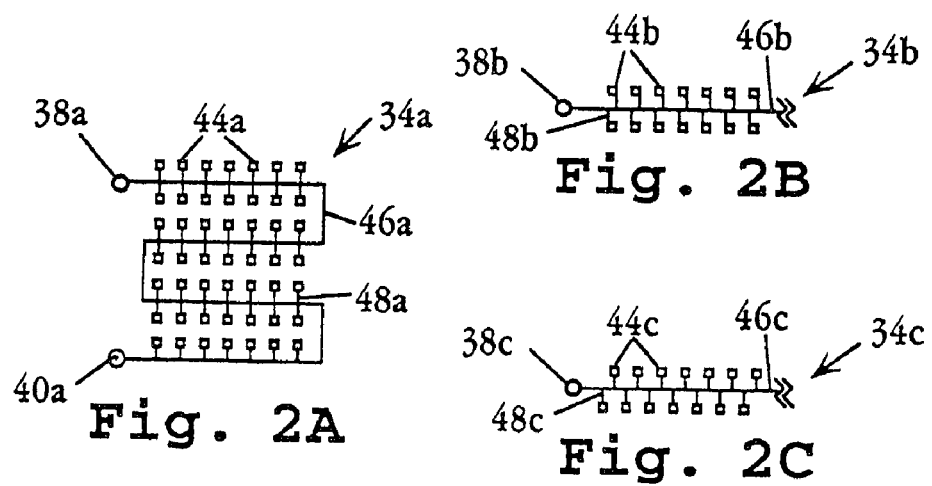
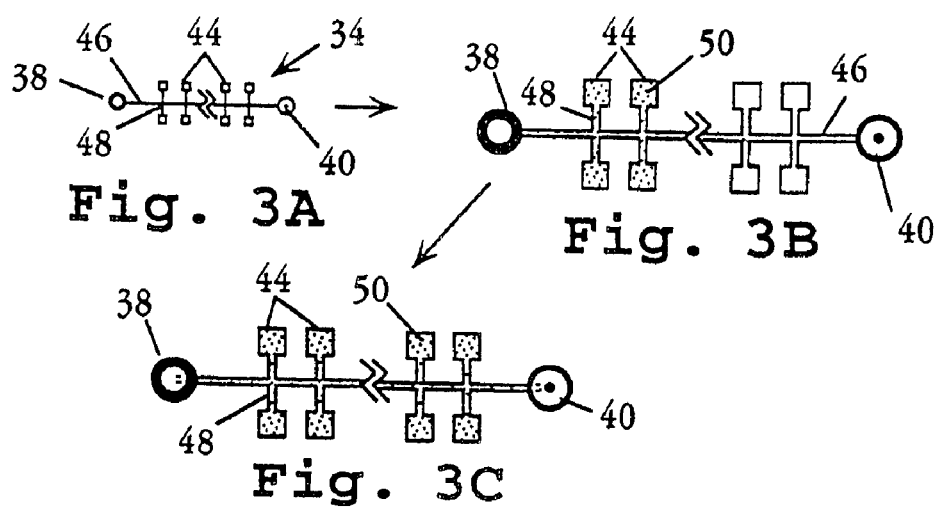

DEVICE AND METHOD FOR MULTIPLE ANALYTE DETECTION

This application is a continuation application of U.S. patent application Ser. No. 11/029,968, filed Jan. 5, 2005, now U.S. Pat. No. 7,244,622, which is a continuation application of U.S. patent application Ser. No. 09/628,076, filed Jul. 28, 2000, now U.S. Pat. No. 7,235,406, which is a continuation application of U.S. patent application Ser. No. 08/831,983, filed Apr. 2, 1997, now U.S. Pat. No. 6,126,899, which claims the benefit of prior Provisional Application No. 60/014,712, filed Apr. 3, 1996, all of which are incorporated herein in their entireties by reference.

FIELD OF THE INVENTION

The present invention relates to devices and methods for detecting or quantifying one or more selected analytes in a sample.

REFERENCES

Ausubel, F. M., et al., *Current Protocols in Molecular Biology*, John Wiley & Sons, Inc., Media, Pa.
Bergot, J. B., et al., PCT Pub. No. WO 91/05060 (1991).
Blake, et al., *Biochemistry* 24:6132 (1985a).
Blake, et al., *Biochemistry* 24:6139 (1985b).
Buchardt, O., et al., PCT Pub. No. WO 92/20703 (1992).
Froehler, et al., *Nucl. Acids Res.* 16:4831 (1988).
Fung, S., et al., EPO Pub. No. 233,053 A2 (1987).
Higuchi, R., et al., *Bio/Technology* 10:413 (1992).
Higuchi, R., et al., *Bio/Technology* 11:1026 (1993).
Ishiguro, T., et al., *Anal. Biochem.* 229:207 (1995).
Kornberg, A., et al., *DNA Replication*, pp 46-47, W.H. Freeman and Co., New York (1992).
Landegren, U., et al., *Science* 241:1077 (1988).
Lee, L. G., et al. *Nucl. Acids Res.* 21:3761 (1993).
Livak, K. J., et al. *PCR Methods and Applications* 4:357 (1995).
Menchen, S. M., et al., U.S. Pat. No. 5,188,934 (1993).
Menchen, S. M., et al., PCT Pub. No. WO 94/05688 (1994).
Miller, P. S., et al, *Biochemistry* 18:5134 (1979).
Miller, P. S., et al., *J. Biol. Chem.* 255:6959 (1980).
Miller, P. S., et al., *Bioconj. Chem.* 1:187 (1990).
Mullis, K., U.S. Pat. No. 4,683,202 (1987).
Murakami, et al., *Biochemistry* 24:4041 (1985).
Saiki, R. K., et al., *Science* 230:1350 (1985).
Sambrook, J., et al., *Molecular Cloning, 2nd Ed.*, Cold Spring Harbor Laboratory Press, NY (1989).
Segev, D., PCT Pub. No. WO 90/01069 (1990).
Segev, D., "Amplification of Nucleic Acid Sequences by the Repair Chain Reaction" in *Nonradioactive Labeling and detection of Biomolecules*, C. Kessler (Ed.), Springer Laboratory, Germany (1992).
Stirchak, E. P., et al., *Org. Chem.* 52:4202 (1987).
Sze, S. M., ed., *VLSI Technology*, 2nd Ed., McGraw-Hill Pub., New York, N.Y. (1988).
Ullman, E. F., U.S. Pat. No. 4,161,515 (1979).
Ullman, E. F., et al., U.S. Pat. No. 4,261,968 (1981).
Whiteley, N. M., et al., U.S. Pat. No. 4,883,750 (1989).
Winn-Deen, E., et al., *Clin. Chem.* 37: 1522 (1991).
Yoshida, et al., U.S. Pat. No. 4,233,401 (1980).

BACKGROUND OF THE INVENTION

Biochemical testing is becoming an increasingly important tool for detecting and monitoring diseases. While tests have long been known for obtaining basic medical information such as blood type and transplant compatibility, for example, advances in understanding the biochemistry underlying many diseases have vastly expanded the number of tests which can be performed. Thus, many tests have become available for various analytical purposes, such as detecting pathogens, diagnosing and monitoring disease, detecting and monitoring changes in health, and monitoring drug therapy.

An important obstacle which has limited exploitation of many biochemical tests has been cost. Simultaneous testing of multiple samples for a single analyte has provided some savings. However, simultaneous assays for a large number of analytes within a single sample have been less practical because of the need for extended sample manipulation, multiple test devices, multiple analytical instruments, and other drawbacks.

Ideally, a method for analyzing an individual sample using a single test device should provide diagnostic information for a large number of potential analytes while requiring a small amount of sample. The device should be small in size while providing high-sensitivity detection for the analytes of interest. The method should also require minimal sample manipulation. Preferably, the device will include pre-dispensed reagents for specific detection of the analytes.

SUMMARY OF THE INVENTION

The present invention is directed generally to a method and device for simultaneously testing a sample for the presence, absence, and/or amount of one or more selected analytes.

The invention includes, in one aspect, a device for detecting or quantitating one or more of a plurality of different analytes in a liquid sample. The device includes a substrate which defines a sample-distribution network having (i) a sample inlet, (ii) one or more detection chambers, and (iii) channel means providing a dead-end fluid connection between each of the chambers and the inlet. Preferably, each chamber includes an analyte-specific reagent effective to react with a selected analyte that may be present in the sample, and detection means for detecting the signal.

In one embodiment, the detection means for each chamber includes an optically transparent window through which the signal can be detected optically. In another embodiment, the detection means includes a non-optical sensor for detecting the signal.

The channel means of the device may be configured in numerous ways. For example, in one embodiment, the channel means includes a single channel to which the detection chambers are connected by dead-end fluid connections. In a second embodiment, the channel means includes at least two different channels, each connected to a different group of detection chambers. In yet another embodiment, the channel means includes an individual channel for each detection chamber.

The device may include a vacuum port for placing the detection chambers under vacuum prior to the addition of sample. In one embodiment, the vacuum port is connected to the channel means at a site between, and in fluid communication with, the sample inlet and the detection chambers. In another embodiment, the vacuum port is connected to the channel means at a site downstream of the detection chambers. In this configuration, the vacuum port is additionally useful for removing liquid from the channel means after the detection chambers have been filled, to help isolate the detection chambers from one another and further reduce cross-contamination.

The vacuum port may be incorporated in a multi-port valve (e.g., a 3-way valve) that permits the network and associated detection chambers to be exposed alternately to a vacuum source, the sample inlet, and a vent or selected gas source.

Alternatively, the device of the invention is prepared and sealed under vacuum when manufactured, so that a vacuum port is unnecessary.

According to an important feature of the invention, the device is capable of maintaining a vacuum within the sample-distribution network (low internal gas pressure, relative to the external, ambient pressure outside the device) for a time sufficient to allow a sample to be drawn into the network and distributed to the detection chambers by vacuum action. For this purpose, the sample-distribution network may include a vacuum reservoir in fluid communication with, and downstream of, the detection chambers, for preventing the build-up of back-pressure in the network while the detection chambers are successively filled.

In one embodiment, the vacuum reservoir includes a non-flowthrough cavity connected downstream of the last-filled detection chamber, for accumulating residual gas displaced from the inlet and channel means. In another embodiment, the reservoir comprises the terminal end of the channel means connected to a vacuum source, allowing residual gas displaced by the sample to be removed continuously until sample loading is complete.

The analyte-specific reagents in the detection chambers may be adapted to detect a wide variety of analyte classes, including polynucleotides, polypeptides, polysaccharides, and small molecule analytes, for example. In one embodiment, the analytes are selected-sequence polynucleotides, and the analyte-specific reagents include sequence-selective reagents for detecting the polynucleotides. The polynucleotide analytes are detected by any suitable method, such as polymerase chain reaction, ligase chain reaction, oligonucleotide ligation assay, or hybridization assay.

In one particular embodiment, for polynucleotide detection, the analyte-specific reagents include an oligonucleotide primer pair suitable for amplifying, by polymerase chain reaction, a target polynucleotide region in the selected analyte which is flanked by sequences complementary to the primer pair. The presence of target polynucleotide, as indicated by successful amplification, is detected by any suitable means.

In another embodiment, the analyte-specific reagents in each detection chamber include an antibody specific for a selected analyte-antigen. In a related embodiment, when the analyte is an antibody, the analyte-specific detection reagents include an antigen for reacting with a selected analyte antibody which may be present in the sample.

In yet another embodiment, the device includes means for regulating the temperatures of the detection chambers, preferably providing temperature control between 0 EC and 100 EC, for promoting the reaction of the sample with the detection reagents. In one preferred embodiment, the temperature regulating means includes a conductive heating element for each detection chamber, for rapidly heating the contents of the chamber to a selected temperature. The temperature control means is preferably adapted to regulate the temperatures of the detection chambers, for heating and cooling the chambers in accordance with a selected assay protocol.

The device may be manufactured and packaged so that the sample-distribution network (e.g., sample inlet, detection chambers, and channel means) is provided under vacuum, ready for immediate use by the user. Alternatively, the sample-distribution network is provided under atmospheric pressure, so that the evacuation step is carried out by the end-user prior to sample loading.

The invention also includes a substrate containing a plurality of sample-distribution networks as described above, for testing a single sample or a plurality of samples for selected analytes.

In another aspect, the invention includes a method of making a device such as described above.

In another aspect, the invention includes a method for detecting or quantitating a plurality of analytes in a liquid sample. In the method, there is provided a device of the type described above, wherein the interior of the network is placed under vacuum. A liquid sample is then applied to the inlet, and the sample is allowed to be drawn into the sample-distribution network by vacuum action, delivering sample to the detection chambers. The delivered sample is allowed to react with the analyte-specific reagent in each detection chamber under conditions effective to produce a detectable signal when the selected analyte is present in the sample. The reaction chambers are inspected or analyzed to determine the presence and/or amount of the selected analytes in the sample.

The device of the invention may also be provided as part of a kit which additionally includes selected reagents, sample preparation materials if appropriate, and instructions for using the device.

These and other objects and features of the invention will be more apparent from the following detailed description when read in light with the accompanying drawings.

BRIEF DESCRIPTION OF THE DRAWINGS

FIGS. 1A and 1B show a plan view (1A) and perspective view (1B) of an exemplary assay device in accordance with the invention;

FIGS. 2A-2C illustrate several exemplary sample distribution network configurations in accordance with the invention;

FIGS. 3A-3C illustrates a time sequence for the filling of the detection chambers of a sample-distribution network with fluid sample;

DETAILED DESCRIPTION OF THE INVENTION

Definitions

Figure 4:
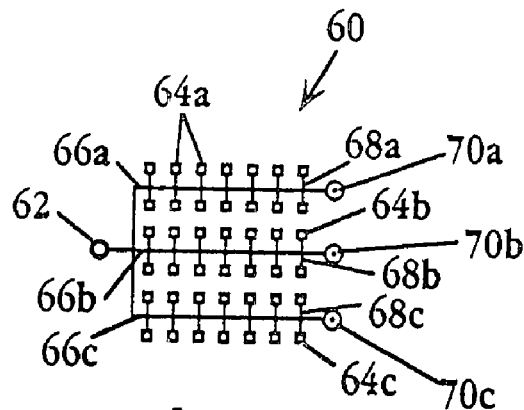
FIG. 4 illustrates a sample-distribution network containing three sample delivery channels for delivering sample to three different sets of detection chambers.

The following terms and phrases as used herein are intended to have the meanings below.

"Dead-end fluid connection between a detection chamber and a sample inlet" refers to a fluid connection which provides the sole fluid access to a detection chamber, such that fluid cannot enter or exit the detection chamber by any other way than through the dead-end fluid connection.

In particular, "dead-end fluid connection" refers to a channel whose cross-section is sufficiently narrow to preclude bi-directional fluid flow through the channel. That is, liquid cannot flow through the channel in one direction while air or another liquid is flowing through the channel in the opposite direction.

As used herein, "microdevice" means a device in accordance with the invention.

Assay Device

In one aspect, the present invention provides a device which is useful for testing one or more fluid samples for the presence, absence, and/or amount of one or more selected analytes. The device includes a substrate which defines a sample-distribution network having (i) a sample inlet, (ii) one or more detection chambers (preferably a plurality of detection chambers), and (iii) channel means providing a dead-end fluid connection between each of the chambers and the inlet. Each chamber includes an analyte-specific reagent effective to react with a selected analyte that may be present in such sample.

In one embodiment, the substrate also provides, for each chamber, an optically transparent window through which analyte-specific reaction products can be detected. In another embodiment, the detection means for each chamber comprises a non-optical sensor for signal detection.

The present invention provides a number of advantages in an assay for multiple analytes in a sample, as will be discussed below. In particular, the invention facilitates the transition from a macro size sample to a micro-sized sample, wherein the device of the invention provides one-step metering of reagents and sample in a multi-analyte detection assay.

Network Configurations

FIGS. 1A and 1B show a plan view and perspective view, respectively, of an exemplary assay device 30 in accordance with the invention. Device 30 includes a substrate 32 which defines a sample-distribution network 34. With reference to FIG. 1B, the device also includes mount 36 containing a sample inlet 38 and optionally, vacuum port means 40 which is located downstream of the detection chambers.

Inlet 38 may be adapted to form a vacuum-tight seal with the end of a syringe, for sample loading, or with a multi-port valve to provide fluid communication with the sample and one or more liquid or gaseous fluids. The inlet may further include a septum cap, if desired, for maintaining the network under vacuum and allowing introduction of sample by canula or needle.

Vacuum port 40 may be adapted for connection to a vacuum source, such as a vacuum pump. The vacuum connection may include a valve for closing off the sample-distribution network from the vacuum source, or a multi-port valve for connection to a vacuum source and one or more selected gas supplies.

Substrate 30 further provides indentations or holes 42, which may be arranged asymmetrically as illustrated in FIG. 1A, to engage corresponding pins or protrusions in a device-holder, not shown, to immobilize and orient the device for analysis.

As noted in the Summary of the Invention, the sample-distribution network of the invention may utilize any of a number of different channel configurations, or channel means, for delivering sample to the individual detection chambers. With reference to FIG. 2A, distribution network 34a includes sample inlet 38a, a plurality of detection chambers 44a, channel means comprising a single channel 46a to which the detection chambers are each connected by dead-end fluid connections 48a, and a vacuum port 40a. The detection chambers are distributed on either side of channel 46a, with the fluid connections branching off in pairs from opposite sides of the channel. FIG. 2B shows a portion of an alternative network 34b having an inlet 38b and detection chambers 44b, wherein fluid connections 48b branch off from channel 46b in a staggered manner.

The detection chambers in the device of the invention may be arranged to form a repeating 2-dimensional array which facilitates indexing and identification of the various chambers, as well as allowing rapid measurement of an optical signal produced by each chamber upon reaction with the sample, if optical detection is used.

FIGS. 2A-2B, for example, show networks in which the detection chambers are arranged in rows and columns along perpendicular axes, allowing the chambers to be identified by X and Y indices if desired. This type of array (a perpendicular array) also facilitates successive interrogations of the chambers in a chamber-by-chamber analysis mode. However, other arrangements may be used, such as a staggered or a close-packed hexagonal array. FIG. 2C, for example, shows part of a network 34c having inlet 38c and an array of staggered detection chambers 44c. The detection chambers are connected to a common delivery channel 46c by fluid connections 48c.

The device may also include identifying symbols adjacent the detection chamber to facilitate identification or confirmation of the analytes being detected.

Preferably, the detection chambers of the device are each provided with analyte-specific reagents which are effective to react with a selected analyte which may be present in the sample, as discussed further below. Reaction of the sample with the analyte-specific reagents results in production of a detectable signal which indicates that the selected analyte is present.

According to an important feature of the invention, the sample is delivered to the detection chambers by vacuum action. Prior to loading with sample, the interior of the sample-distribution network is placed under vacuum so that the residual gas pressure in the network is substantially below atmospheric pressure (i.e., substantially less than 760 mm Hg). One advantage of this feature of the invention is that a pump for pushing fluid through the network is not required. Instead, the device exploits ambient atmospheric pressure to push the sample through the sample inlet and into the sample-distribution network. This allows the sample to be delivered quickly and efficiently to the detection chambers.

FIGS. 3A-3C illustrate the filling process for a sample-distribution network 34 in accordance with FIG. 2A. The network includes sample inlet 38, detection chambers 44, and sample delivery channel 46 which is connected to the various detection chambers by dead-end fluid connections 48. The network further includes a vacuum reservoir 40 at the terminus of the delivery channel. A plurality of the detection chambers 44 contain dried detection reagents for detecting a different selected analyte in each chamber, with one or more chambers optionally being reserved as controls.

FIG. 3A shows the device before sample loading is initiated. The network is evacuated to establish an internal pressure within the network that is substantially below atmospheric pressure (e.g., 1 to 40 mm Hg). The interior of the network should also be substantially liquid-free to minimize vapor pressure problems. FIG. 3B shows the network after sample fluid 50 has entered the network through inlet 38 (FIG. 3B). As the sample moves through channel 46, the sample sequentially fills each of the detection chambers (FIG. 3B) until all of the chambers have been filled (FIG. 3C). With continued reference to FIG. 3C, once the detection chambers have all been filled, sample fluid may continue to flow through channel 46 into vacuum reservoir 40 until the reservoir becomes full or the flow is otherwise terminated (e.g., by closing a valve associated with the vacuum reservoir).

According to one advantage of the invention, continued sample flow through the channel means does not substantially disturb the contents of the detection chambers that have already been filled, because further flow into or out of each filled detection chamber is restricted by the dead-end fluid connections, such as connections 48. Cross-contamination between different detection chambers is therefore reduced, so that erroneous signals due to cross-contamination can be avoided. A further advantage of the invention is that the sample can be mixed with the analyte-specific detection reagents and detected all in the same chamber, without requiring movement of the sample from each chamber to another site. Moreover, since the sample and detection reagents can remain in the chamber for signal detection, the detection reagents need not be immobilized on or adhered to the inner surfaces of the detection chambers.

The components of the sample-distribution network are designed to ensure that an adequate volume of sample will be delivered to the detection chambers to allow accurate analyte detection and/or quantitation. In general, the percent-volume of a detection chamber that must be occupied by the sample will vary according to the requirements of the reagents and the detection system used. Typically, the volume-percent will be greater than 75%, preferably greater than 90%, and more preferably greater than 95%. In assay formats in which the detection chambers are heated, particularly to temperatures of between about 60 EC and about 95 EC, the volume-percent filling of the chambers is preferably greater than 95%, and more preferably is at least 99%.

The degree to which the detection chambers are filled with sample will generally depend upon (1) the initial ratio of the external (atmospheric) pressure to the initial pressure within the network, (2) the individual and total volumes defined by the detection chambers, (3) the volume defined by the channel means, and (4) the nature of the network downstream of the last detection chamber.

For example, in the case of a detection chamber which is nearest the sample inlet, and which will be filled first, the percentage occupancy (volume-percent) of sample fluid in the chamber after sample loading ($V_{s,\%}$) will be related to the external atmospheric pressure ($P_{ext}$) and the initial internal pressure within the network before sample loading ($P_{int}$) by the expression:

$$V_{s,\%} \cdot (P_{ext})/(P_{ext}+P_{int})$$

Thus, if the initial pressure within the network ($P_{int}$) is 10 mm Hg, and the external pressure ($P_{ext}$) is 760 mm Hg, about 99% of the first detection chamber will be filled with sample fluid ($V_{s,\%} \cdot 99\%$), with the remaining volume ($\cdot 1.3\%$) being filled by residual gas (e.g., air) displaced by the sample. (This calculation assumes that, by the time the sample reaches the chamber, the internal network pressure has not increased appreciably due to displacement of gas upstream of the chamber.) Similarly, if $P_{ext}$ is 760 mm Hg and $P_{int}$ is only 40 mm Hg, the volume-percent of the chamber that becomes occupied with sample will still be very high (about 95%).

It will be appreciated that as the sample fluid reaches and fills successive detection chambers, the residual gas displaced from the channel means will gradually accumulate in the remaining network volume, so that the internal pressure will gradually increase. The resultant increase in back-pressure can lead to a reduction in $V_{s,\%}$ for each successive chamber, with $V_{s,\%}$ for the last-filled detection chamber being significantly lower than the $V_{s,\%}$ for the first-filled chamber.

To help avoid this problem, the dimensions of the channel and dead-end fluid connections are preferably selected to define a total volume that is substantially less than the total volume defined by the detection chambers. Preferably, the collective volume of the channel means is less than 20% of the total collective volume of the detection chambers, and more preferably less than 5%. Similarly, the volume of each dead-end fluid connection should be substantially less than the volume of the associated detection chamber. Preferably, the volume of each dead-end connection is less than 20%, preferably less than 10%, and more preferably less than 5% of the volume of the associated detection chamber.

The problem of back-pressure can be further diminished by including a vacuum reservoir downstream of the last detection chamber to be filled. In one embodiment, the vacuum reservoir is a non-flowthrough cavity in which gas displaced by the sample fluid can collect. The volume of the reservoir will vary according to the configuration and needs of the particular device. For example, the volume of the reservoir can be selected to be equal in volume to one or more detection chambers volumes, or alternatively, is one- to five-fold as great as the total collective volume of the channel means.

In another embodiment, the vacuum reservoir is connected to a vacuum source, so that residual gas can be removed continuously until sample loading into the detection chambers is complete, as discussed further below.

FIG. 4 shows another sample-distribution network in accordance with the invention, wherein the channel means of the network includes at least two different sample delivery channels, each connected to a different group of detection chambers. FIG. 4 shows a sample-distribution network 60 having a sample inlet 62, three different groups of detection chambers 64a, 64b, and 64c, and channel means 66 which include corresponding channels 66a, 66b, and 66c associated with the three chamber groups. The chambers are connected to channels 66a-66c via dead-end fluid connections 68a-68c, which provide uni-directional flow of the sample into the detection chambers.

One advantage of using multiple delivery channels is that the time needed to fill the detection chambers with the sample can be significantly reduced relative to the time needed to fill the same number of detection chambers using a single delivery channel. For example, the loading time for a network in accordance with FIG. 4 will be about one-third of that needed to fill an identical number of detection chambers via the single channel format illustrated in FIG. 2A, all other factors being equal. More generally, for a given number of detection chambers, the filling time will vary inversely with the number of delivery channels used.

The sample-distribution network in FIG. 4 further includes separate vacuum reservoirs 70a-70c which are connected to the termini of sample delivery channels 66a-66c, downstream of the detection chambers. The vacuum chambers are dimensioned to help maintain a low internal gas pressure during sample loading.

Figure 5:
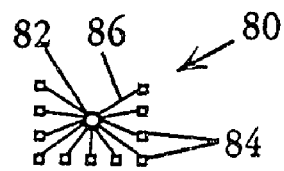
FIG. 5 illustrates a sample-distribution network having a separate delivery channel for each detection chamber.

In another embodiment, the channel means includes an individual channel for each detection chamber, as illustrated in FIG. 5. Network 80 includes an inlet 82, detection chambers 84, and associated with each detection chamber, a dead-end fluid connection 86, which may also be referred to as channel means, for delivering sample to each chamber. Each dead-end fluid connection is dimensioned to define a volume that is substantially less than the volume of the associated detection chamber, to ensure that each detection chamber is sufficiently filled with sample. This embodiment provides rapid filling of the detection chambers with minimal cross-contamination.

The device of the invention may also include a vacuum port communicating with the sample-distribution network, for applying a vacuum to the network before or during sample loading. In one embodiment, the vacuum port is connected to the channel means at a site between, and in fluid communication with, the sample inlet and the detection chambers. An illustration of this can be found in FIG. 9. The vacuum port thus provides a convenient way to reduce the internal pressure within the network to a selected residual pressure prior to sample loading. In particular, when the sample is introduced into the network using a syringe barrel connected to the sample inlet, the vacuum port can be used to remove air from the space between the syringe and the inlet, before the sample is admitted into the network.

Figure 6A:
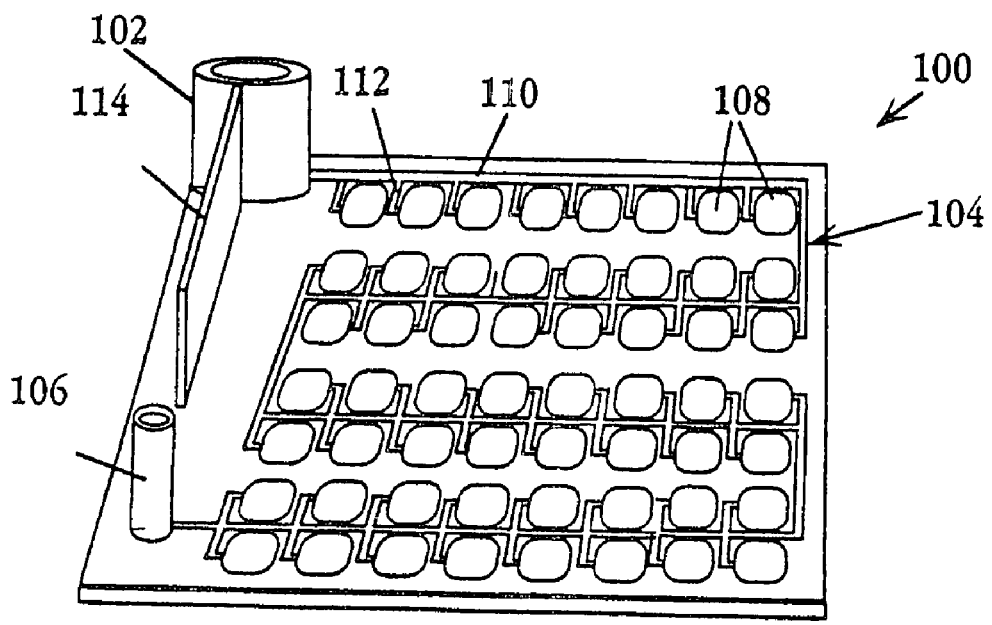
FIGS. 6A-6C illustrate selected features of another sample-distribution network in accordance with the invention; the device is shown in plan view (6A), perspective view (6B), with a portion of the sample distribution network of the device shown in FIG. 6C.

In another embodiment, the vacuum port is connected to the channel means at a site downstream of the sample inlet and detection chambers (e.g., FIG. 6A). In this configuration, the vacuum port may additionally be used to remove liquid from the channel means after the detection chambers have been filled, to help isolate the detection chambers from one another and further reduce cross-contamination. In this configuration, the vacuum port constitutes a part of the vacuum reservoir described above, where the reservoir includes a vacuum source linked to the terminal end of a sample delivery channel. The vacuum port may be kept open to the network during sample loading, to continuously remove residual gas from the network until all of the detection chambers have been filled.

The vacuum port may include a multi-port valve (e.g., 3-way valve) that permits the network and associated detection chambers to be exposed alternately to a vacuum source, the sample inlet, and a vent or gas source. Such a valve may be used to alternately expose the network to vacuum and a selected gas source, to replace residual air with the selected gas. Such gas replacement in the network may be useful to remove molecular oxygen ($O_2$) or other atmospheric gases which might otherwise interfere with the performance of the detection reagents.

Argon and nitrogen are inert gases which may be suitable for most situations. Another gas which may be used is carbon dioxide ($CO_2$), which is highly soluble in water due to its ability to form carbonate and bicarbonate ions. When the sample fluid is an aqueous solution, bubbles of carbon dioxide which may form in the network during sample loading may be eliminated via dissolution in the sample fluid. The degree of sample filling in the detection chambers is therefore enhanced. Of course, carbon dioxide should not be used if it interferes with the detection reagents.

A multi-port valve such as noted above can also be used to supply a gas which is required for detection of the selected analytes. For example, it may be desirable to provide molecular oxygen or ozone where the detection reagents involve an oxidation reaction. Other gases, such as hydrocarbons (ethylene, methane) or nitrogenous gases, may also be introduced as appropriate.

Device Fabrication

The device of the invention is designed to allow testing of a sample for a large number of different analytes by optical analysis, using a device that is compact and inexpensive to prepare. Generally, the device will be no larger in cross-section than the cross-section of a standard credit card ($\leq 5$ cm×10 cm), and will have a thickness (depth) of no greater than 2 cm. More preferably, the device occupies a volume of no greater than about 5×5×1 cm, excluding attachments for the sample inlet and any vacuum port. More preferably, the device has dimensions of no greater than about 3 cm×2 cm×0.3 cm. Devices smaller than this are also contemplated, bearing in mind that the device should provide adequate sensitivity and be easy for the end-user to handle.

The detection chambers in the device are generally designed to be as small as possible, in order to achieve high density of detection chambers. The sizes and dimensions of the chambers will depend on a number of considerations. When signal detection is by optical means, the overhead cross-section of each chamber must be large enough to allow reliable measurement of the signal produced when the selected analyte is present in the sample. Also, the depths of the chambers can be tailored for the particular optical method used. For fluorescence detection, thin chambers may be desirable, to minimize quenching effects. For absorbance or chemiluminescence detection, on the other hand, a thicker chamber may be appropriate, to increase the detection signal.

It will be appreciated that while the figures in the attached drawings show chambers having square-shaped overhead cross-sections, other geometries, such as circles or ovals, may also be used. Similarly, the channels in the network may be straight or curved, as necessary, with cross-sections that are shallow, deep, square, rectangular, concave, or V-shaped, or any other appropriate configuration.

Typically, the detection chambers will be dimensioned to hold from 0.001 μL to 10 μL of sample per chamber, and, more preferably between 0.01 μL and 2 μL. Conveniently, the volume of each detection chamber is between about 0.1 μL and 1 μL, to allow visual confirmation that the chambers have been filled. For example, a chamber having a volume of 0.2 μL may have dimensions of 1 mm×1 mm×0.2 mm, where the last dimension is the chamber's depth.

The sample delivery channels are dimensioned to facilitate rapid delivery of sample to the detection chambers, while occupying as little volume as possible. Typical cross-sectional dimensions for the channels will range from 5 μm to about 250 μm for both the width and depth. Ideally, the path lengths between chambers will be as short as possible to minimize the total channel volume. For this purpose (to minimize volume), the network is preferably substantially planar, i.e., the channel means and detection chambers in the device intersect a common plane.

The substrate that defines the sample-distribution network of the invention may be formed from any solid material that is suitable for conducting analyte detection. Materials which may be used will include various plastic polymers and copolymers, such as polypropylenes, polystyrenes, polyimides, and polycarbonates. Inorganic materials such as glass and silicon are also useful. Silicon is especially advantageous in view of its high thermal conductivity, which facilitates rapid heating and cooling of the device if necessary. The substrate may be formed from a single material or from a plurality of materials.

The sample-distribution network is formed by any suitable method known in the art. For plastic materials, injection molding will generally be suitable to form detection chambers and connecting channels having a desired pattern. For silicon, standard etching techniques from the semiconductor industry may be used, as described in Sze (1988), for example.

Typically, the device substrate is prepared from two or more laminated layers, as will be discussed below with reference to FIGS. 6A-6C to 8. For optical detection, the device will include one or more layers which provide an optically transparent window for each detection chamber, through which the analyte-specific signal is detected. For this purpose, silica-based glasses, quartz, polycarbonate, or an optically transparent plastic layer may be used, for example. Selection of the particular window material depends in part on the optical properties of the material. For example, in a fluorescence-based assay, the material should have low fluorescence emission at the wavelength(s) being measured. The window material should also exhibit minimal light absorption for the signal wavelengths of interest.

Other layers in the device may be formed using the same or different materials. Preferably, the layer or layers defining the detection chambers are formed predominantly from a material that has high heat conductivity, such as silicon or a heat-conducting metal. The silicon surfaces which contact the sample are preferably coated with an oxidation layer or other suitable coating, to render the surface more inert. Similarly, where a heat-conducting metal is used in the substrate, the metal can be coated with an inert material, such as a plastic polymer, to prevent corrosion of the metal and to separate the metal surface from contact with the sample. The suitability of a particular surface should be verified for the selected assay.

For optical detection, the opacity or transparency of the substrate material defining the detection chambers will generally have an effect on the permissible detector geometries used for signal detection. For the following discussion, references to the "upper wall" of a detection chamber refer to the chamber surface or wall through which the optical signal is detected, and references to the "lower wall" of a chamber refers to the chamber surface or wall that is opposite the upper wall.

When the substrate material defining the lower wall and sides of the detection chambers is optically opaque, and detection is by absorption or fluorescence, the detection chambers will usually be illuminated and optically scanned through the same surface (i.e., the top surfaces of the chambers which are optically transparent). Thus, for fluorescence detection, the opaque substrate material preferably exhibits low reflectance properties so that reflection of the illuminating light back toward the detector is minimized. Conversely, a high reflectance will be desirable for detection based on light absorption.

When the substrate material defining the upper surface and sides of the detection chambers is optically clear, and detection involves fluorescence measurement, the chambers can be illuminated with excitation light through the sides of the chambers (in the plane defined collectively by the detection chambers in the device), or more typically, diagonally from above (e.g., at a 45 degree angle), and emitted light is collected from above the chambers (i.e., through the upper walls, in a direction perpendicular to the plane defined by the detection chambers). Preferably, the substrate material exhibits low dispersion of the illuminating light in order to limit Rayleigh scattering.

When the entirety of the substrate material is optically clear, or at least the upper and lower walls of the chambers are optically clear, the chambers can be illuminated through either wall (upper or lower), and the emitted or transmitted light is measured through either wall as appropriate. Illumination of the chambers from other directions will also be possible as already discussed above.

With chemiluminescence detection, where light of a distinctive wavelength is typically generated without illumination of the sample by an outside light source, the absorptive and reflective properties of the substrate will be less important, provided that the substrate provides at least one optically transparent window for detecting the signal.

Figure 6B:
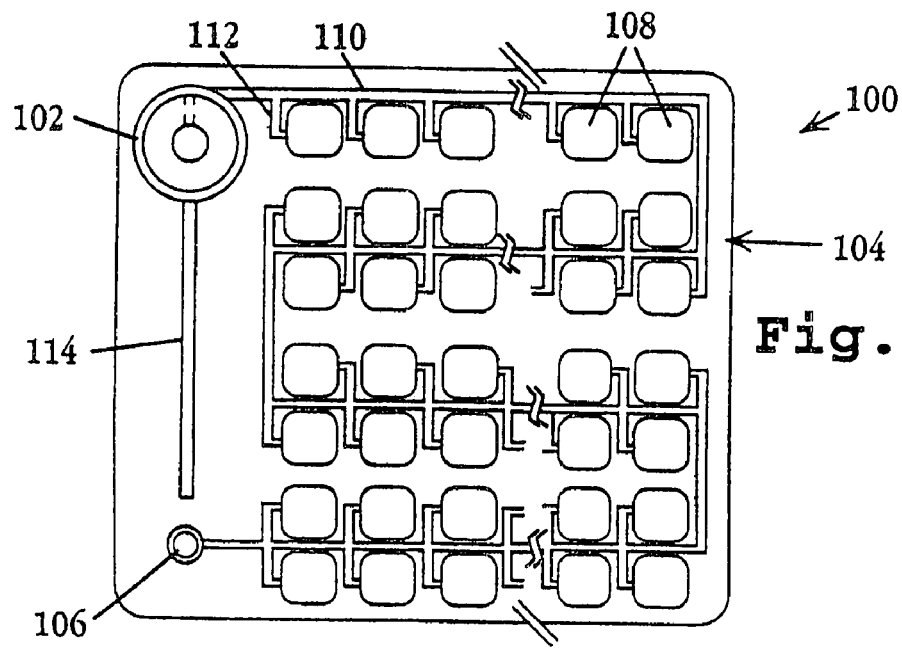
Figure 6C:
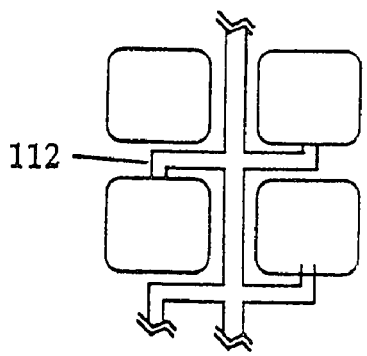

FIGS. 6A-6C illustrate a specific embodiment of a device in accordance with the invention. With reference to FIGS. 6A and 6B, device 100 includes a sample inlet 102, sample-distribution network 104, and vacuum port 106 which is connected to the terminus of network 104. Network 104 includes a perpendicular array of detection chambers 108 (7 rows×8 columns) linked to sample delivery channel 110 via dead-end fluid connections 112. The device further includes vertical panel 114 adjacent sample inlet 102, for attaching an identifying label to the device and as an attachment allowing the user to hold the device.

Figure 7:
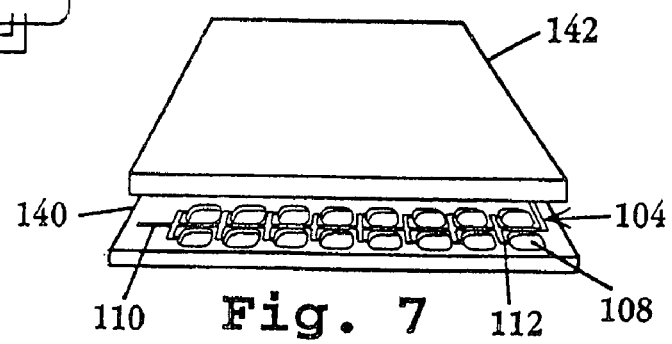
FIG. 7 shows an exploded view of a portion of a device in accordance with the invention.
Figure 8:
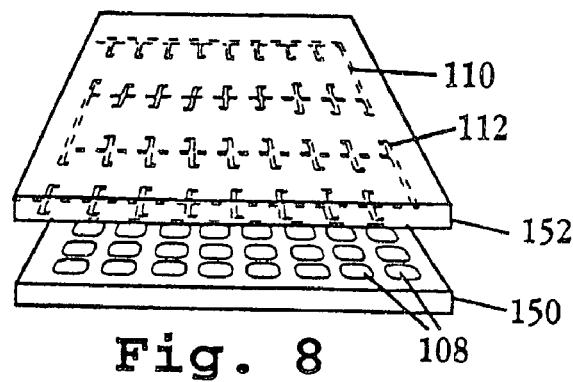
FIG. 8 shows an exploded view of a portion of another device in accordance with the invention.

As can be seen from FIG. 6B, the detection chambers are packed closely together to increase the number of analytes which can be tested in the device. Fluid connections 112 are provided in an L-shaped configuration (FIG. 6C) to impede fluid flow out of the chambers after sample loading, and to help isolate the contents of the chambers from each other. Although the horizontal rows of detection chambers in FIGS. 6A and 6B are shown as being separated from each other by variable vertical spacing (to enhance the clarity of the figures), it will be appreciated that the chambers can be separated by equal distances in both the vertical and ho FIGS. 7 and 8 illustrate two exemplary approaches for forming a testing device in accordance with FIGS. 6A-6B. FIG. 7 shows two substrate layers 140 and 142 which can be brought together to form sample-distribution network 104 (FIG. 6A). The network is defined primarily by substrate layer 140, which contains indentations defining a sample inlet 102 (not shown), a plurality of detection chambers 108, sample delivery channel 110, and dead-end fluid connections 112. Contact of substrate layer 142 with the opposing face of layer 140 completes the formation of network 104.

FIG. 8 shows substrate layers 150 and 152 for forming a network by another approach. Substrate layer 150 contains indentations defining a plurality of detection chambers 108. Substrate layer 152, on the other hand, contains indentations defining sample delivery channel 110 and dead-end fluid connections 112. Network 104 can then be formed by contacting the opposing faces of the two substrate layers as in FIG. 7.

Since the device is designed to provide a vacuum-tight environment within the sample-distribution network for sample loading, and also to provide detection chambers having carefully defined reaction volumes, it is desirable to ensure that the network and associate detection chambers do not leak. Accordingly, lamination of substrate layers to one another should be accomplished so as to ensure that all chambers and channels are well sealed.

In general, the substrate layers can be sealably bonded in a number of ways. Conventionally, a suitable bonding substance, such as a glue or epoxy-type resin, is applied to one or both opposing surfaces that will be bonded together. The bonding substance may be applied to the entirety of either surface, so that the bonding substance (after curing) will come into contact with the detection chambers and the distribution network. In this case, the bonding substance is selected to be compatible with the sample and detection reagents used in the assay. Alternatively, the bonding substance may be applied around the distribution network and detection chambers so that contact with the sample will be minimal or avoided entirely. The bonding substance may also be provided as part of an adhesive-backed tape or membrane which is then brought into contact with the opposing surface. In yet another approach, the sealable bonding is accomplished using an adhesive gasket layer which is placed between the two substrate layers. In any of these approaches, bonding may be accomplished by any suitable method, including pressure-sealing, ultrasonic welding, and heat curing, for example.

The device of the invention may be adapted to allow rapid heating and cooling of the detection chambers to facilitate reaction of the sample with the analyte-detection reagents. In one embodiment, the device is heated or cooled using an external temperature-controller. The temperature-controller is adapted to heat/cool one or more surfaces of the device, or may be adapted to selectively heat the detection chambers themselves.

To facilitate heating or cooling with this embodiment, the substrate material of the test device is preferably formed of a material which has high thermal conductivity, such as copper, aluminum, or silicon. Alternatively, a substrate layer such as layer 140 in FIG. 7 may be formed from a material having moderate or low thermal conductivity, while substrate layer 142 (FIG. 7) is provided as a thin layer, such that the temperature of the detection chambers can be conveniently controlled by heating or cooling the device through layer 142, regardless of the thermal conductivity of the material of layer 142. In one preferred embodiment, layer 142 is provided in the form of an adhesive copper-backed tape.

In an alternative embodiment, means for modulating the temperature of the detection chambers is provided in the substrate of the device itself. For example, with reference to FIG. 7, substrate layer 142 may include resistive traces which contact regions adjacent the reaction chambers, whereby passage of electrical current through the traces is effective to heat or cool the chambers. This approach is particularly suitable for silicon-based substrates, and can provide superior temperature control.

Figure 9:
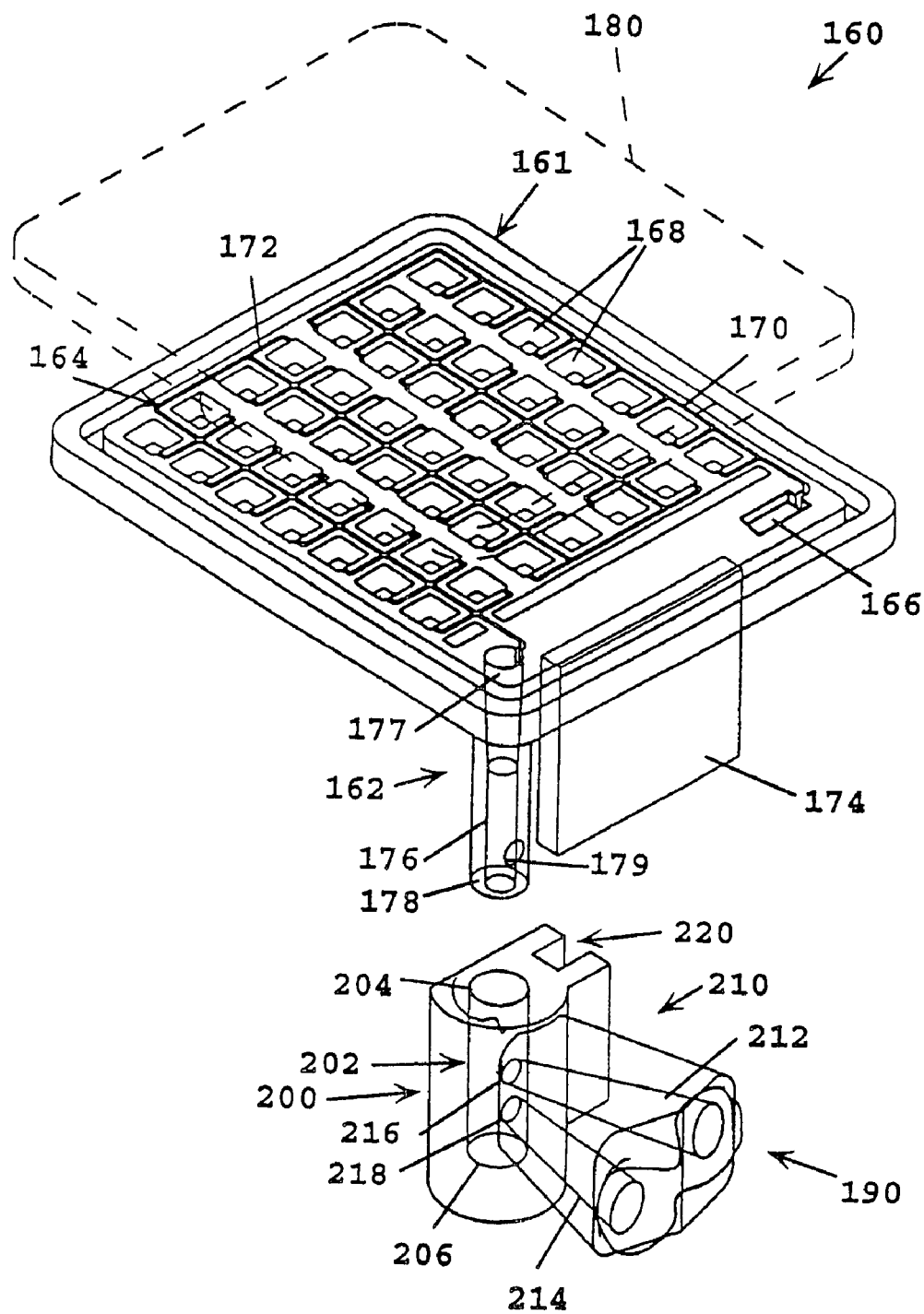
FIG. 9 shows a perspective view of another device in accordance with the invention.

Further illustration of the invention is provided by the device shown in FIG. 9. Device 160 includes a network-defining substrate layer 161 and a flat substrate layer 180 for bonding with and sealing layer 161.

Layer 161 includes sample inlet 162 and indentations defining (i) a sample-distribution network 164 and (ii) vacuum reservoir 166 connected to the terminus of network 164. Network 164 includes a 2-dimensional perpendicular array of detection chambers 168 (7×7) linked to sample delivery channel 170 via dead-end fluid connections 172. The device further includes vertical panel 174 adjacent sample inlet 162, as in FIGS. 6A-6B. Formation of network 164 is completed by contacting the entirety of the upper surface of device 160 with the opposing face of a layer 180, which is preferably provided in the form of a membrane or thin layer.

Device 160 in FIG. 9 is distinguished from device 100 in FIG. 6A in that device 160 includes a vacuum reservoir 166, instead of a vacuum port, at the terminus of delivery channel 170. In addition, sample inlet 162 in device 160 is conveniently adapted to operate in conjunction with inlet fitting 190, so that evacuation of the network and sample loading can be effected from a single site with respect to the network.

Sample inlet 162 includes a hollow inlet cylinder 176 having an open proximal end 177, which connects to network 164, and an open, distal end 178. Cylinder 176 further includes an opening 179 located near the terminus of the distal end.

Inlet fitting 190 includes an inlet cap structure 200 and a port structure 210 appended thereto. Cap structure 200 defines a hollow cylinder 202 having an open, proximal end 204 and a closed, distal end 206. The inner diameter of cylinder 202 is dimensioned to form a vacuum-tight seal when placed over inlet 162. Port structure 210 defines a vacuum port 212 and a sample port 214. Ports 212 and 214 communicate with cylinder 202 via openings 216 and 218, respectively, which are formed in the side of cylinder 202. Fitting 190 additionally includes guide structure 220 for receiving the adjacent edge of panel 174, to orient and guide fitting 190 when fitting 190 is fitted over and slided along inlet 162.

Exemplary dimensions of a device which has been prepared in accordance with FIG. 9 are the following: detection chambers 168, 1.2 mm×1.2 mm×0.75 mm; delivery channel 170, 0.25 mm×0.25 mm (width×depth); dead-end fluid connection 172, 0.25 mm×0.25 mm (width×depth); external dimensions: 22 cm×15 cm×1 mm (dimensions of network-defining portion, excluding inlet 162 and panel 174). Preferably, the detection chambers in the microdevice of the invention have volumes less than 10 μL, less than 2 μL, and most preferably less than or equal to 1 μL.

Device 160 may be prepared under ordinary atmospheric conditions by bonding a polymeric, adhesive-backed substrate layer 180 to the corresponding surface of layer 161, to form a sealed network. Inlet fitting 190 is fitted onto cylinder 176 of inlet 162, such that openings 179 and 216 are aligned with each other. Vacuum port 212 is connected to a vacuum line, and the interior of the network is evacuated for a selected time. The network may be alternately flushed with a selected gas, such as carbon dioxide, and vacuum, as discussed above. During evacuation, sample port 214 is loaded with, or placed in fluid communication with, the fluid sample. Preferably, the sample port is filled so that there is no air between the sample in the sample port and opening 218. Once the network has been evacuated (usually complete within a few seconds), fitting 190 is lowered further towards layer 161 until opening 179 is aligned with sample opening 218, bringing the interior of the network in fluid communication with the sample. The sample fills the chambers rapidly, typically in less than half a second. The detection chambers are filled to a volume-percent of greater than 95%. Excess sample and residual gas collects in reservoir 166.

Once the chambers have filled with sample, fitting 190 is lowered further toward layer 161 in order to seal inlet 162, thereby sealing the interior of the network from the outside atmosphere. The sample is allowed to react with the detection reagents in the detection chambers, during or after which the optical signals produced in the chambers are detected.

Detection Reagents

The detection chamber(s) of the device may be pre-loaded with detection reagents which are specific for the selected analytes of interest. The detection reagents are designed to produce an optically detectable signal via any of the optical methods noted in Section II below.

It will be appreciated that although the reagents in each detection chamber must contain substances specific for the analyte(s) to be detected in the particular chamber, other reagents necessary to produce the optical signal for detection may be added to the sample prior to loading, or may be placed at locations elsewhere in the network for mixing with the sample. Whether particular assay components are included in the detection chambers or elsewhere will depend on the nature of the particular assay, and on whether a given component is stable to drying. In general, it is preferred that as many of the detection reagents as possible are pre-loaded in the detection chambers during manufacture of the device, in order to enhance assay uniformity and minimize the assay steps conducted by the end-user.

The analyte to be detected may be any substance whose presence, absence, or amount is desirable to be determined. The detection means can include any reagent or combination of reagents suitable to detect or measure the analyte(s) of interest. It will be appreciated that more than one analyte can be tested for in a single detection chamber, if desired.

In one embodiment, the analytes are selected-sequence polynucleotides, such as DNA or RNA, and the analyte-specific reagents include sequence-selective reagents for detecting the polynucleotides. The sequence-selective reagents include at least one binding polymer which is effective to selectively bind to a target polynucleotide having a defined sequence.

The binding polymer can be a conventional polynucleotide, such as DNA or RNA, or any suitable analog thereof which has the requisite sequence selectivity. For example, binding polymers which are analogs of polynucleotides, such as deoxynucleotides with thiophosphodiester linkages, and which are capable of base-specific binding to single-stranded or double-stranded target polynucleotides may be used. Polynucleotide analogs containing uncharged, but stereoisomeric methylphosphonate linkages between the deoxyribonucleoside subunits have been reported (Miller, 1979, 1980, 1990, Murakami, Blake, 1985a, 1985b). A variety of analogous uncharged phosphoramidate-linked oligonucleotide analogs have also been reported (Froehler). Also, deoxyribonucleoside analogs having achiral and uncharged intersubunit linkages (Stirchak) and uncharged morpholino-based polymers having achiral intersubunit linkages have been reported (U.S. Pat. No. 5,034,506). Binding polymers known generally as peptide nucleic acids may also be used (Buchardt, 1992). The binding polymers may be designed for sequence specific binding to a single-stranded target molecule through Watson-Crick base pairing, or sequence-specific binding to a double-stranded target polynucleotide through Hoogstein binding sites in the major groove of duplex nucleic acid (Kornberg). A variety of other suitable polynucleotide analogs are also known.

The binding polymers for detecting polynucleotides are typically 10-30 nucleotides in length, with the exact length depending on the requirements of the assay, although longer or shorter lengths are also contemplated.

In one embodiment, the analyte-specific reagents include an oligonucleotide primer pair suitable for amplifying, by polymerase chain reaction, a target polynucleotide region of the selected analyte which is flanked by 3'-sequences complementary to the primer pair. In practicing this embodiment, the primer pair is reacted with the target polynucleotide under hybridization conditions which favor annealing of the primers to complementary regions of opposite strands in the target. The reaction mixture is then thermal cycled through several, and typically about 20-40, rounds of primer extension, denaturation, and primer/target sequence annealing, according to well-known polymerase chain reaction (PCR) methods (Mullis, Saiki).

Typically, both primers for each primer pair are pre-loaded in each of the respective detection chambers, along with the standard nucleotide triphosphates, or analogs thereof, for primer extension (e.g., ATP, CTP, GTP, and TTP), and any other appropriate reagents, such as $MgCl_2$ or $MnCl_2$. A thermally stable DNA polymerase, such as Taq, Vent, or the like, may also be pre-loaded in the chambers, or may be mixed with the sample prior to sample loading. Other reagents may be included in the detection chambers or elsewhere as appropriate. Alternatively, the detection chambers may be loaded with one primer from each primer pair, and the other primer (e.g., a primer common to all of detection chambers) may be provided in the sample or elsewhere.

If the target polynucleotides are single-stranded, such as single-stranded DNA or RNA, the sample is preferably pre-treated with a DNA- or RNA-polymerase prior to sample loading, to form double-stranded polynucleotides for subsequent amplification.

The presence and/or amount of target polynucleotide in a detection chamber, as indicated by successful amplification, is detected by any suitable means. For example, amplified sequences may be detected in double-stranded form by including an intercalating or cross-linking dye, such as ethidium bromide, acridine orange, or an oxazole derivative, for example, which exhibits a fluorescence increase or decrease upon binding to double-stranded nucleic acids (Sambrook, 1989; Ausubel; Higuchi, 1992, 1993; Ishiguro, 1995).

The level of amplification can also be measured by fluorescence detection using a fluorescently labeled oligonucleotide, such as disclosed in Lee et al. (1993) and Livak et al. (1995). In this embodiment, the detection reagents include a sequence-selective primer pair as in the more general PCR method above, and in addition, a sequence-selective oligonucleotide (FQ-oligo) containing a fluorescer-quencher pair. The primers in the primer pair are complementary to 3'-regions in opposing strands of the target analyte segment which flank the region which is to be amplified. The FQ-oligo is selected to be capable of hybridizing selectively to the analyte segment in a region downstream of one of the primers and is located within the region to be amplified.

The fluorescer-quencher pair includes a fluorescer dye and a quencher dye which are spaced from each other on the oligonucleotide so that the quencher dye is able to significantly quench light emitted by the fluorescer at a selected wavelength, while the quencher and fluorescer are both bound to the oligonucleotide. The FQ-oligo preferably includes a 3'-phosphate or other blocking group to prevent terminal extension of the 3'-end of the oligo.

The fluorescer and quencher dyes may be selected from any dye combination having the proper overlap of emission (for the fluorescer) and absorptive (for the quencher) wavelengths while also permitting enzymatic cleavage of the FQ-oligo by the polymerase when the oligo is hybridized to the target. Suitable dyes, such as rhodamine and fluorescein derivatives, and methods of attaching them, are well known and are described, for example, in Menchen et al. (1993, 1994), Bergot et al. (1991), and Fung et al. (1987).

The fluorescer and quencher dyes are spaced close enough together to ensure adequate quenching of the fluorescer, while also being far enough apart to ensure that the polymerase is able to cleave the FQ-oligo at a site between the fluorescer and quencher. Generally, spacing of about 5 to about 30 bases is suitable, as generally described in Livak et al. (1995). Preferably, the fluorescer in the FQ-oligo is covalently linked to a nucleotide base which is 5' with respect to the quencher.

In practicing this approach, the primer pair and FQ-oligo are reacted with a target polynucleotide (double-stranded for this example) under conditions effective to allow sequence-selective hybridization to the appropriate complementary regions in the target. The primers are effective to initiate extension of the primers via DNA polymerase activity. When the polymerase encounters the FQ-probe downstream of the corresponding primer, the polymerase cleaves the FQ-probe so that the fluorescer is no longer held in proximity to the quencher. The fluorescence signal from the released fluorescer therefore increases, indicating that the target sequence is present.

One advantage of this embodiment is that only a small proportion of the FQ-probe need be cleaved in order for a measurable signal to be produced. In a further embodiment, the detection reagents may include two or more FQ-oligos having distinguishable fluorescer dyes attached, and which are complementary for different-sequence regions which may be present in the amplified region, e.g., due to heterozygosity (Lee, 1993).

In another embodiment, the detection reagents include first and second oligonucleotides effective to bind selectively to adjacent, contiguous regions of a target sequence in the selected analyte, and which may be ligated covalently by a ligase enzyme or by chemical means (Whiteley, 1989; Landegren, 1988) (oligonucleotide ligation assay, OLA). In this approach, the two oligonucleotides (oligos) are reacted with the target polynucleotide under conditions effective to ensure specific hybridization of the oligo-nucleotides to their target sequences. When the oligonucleotides have base-paired with their target sequences, such that confronting end subunits in the oligos are basepaired with immediately contiguous bases in the target, the two oligos can be joined by ligation, e.g., by treatment with ligase. After the ligation step, the detection wells are heated to dissociate unligated probes, and the presence of ligated, target-bound probe is detected by reaction with an intercalating dye or by other means.

The oligos for OLA may also be designed so as to bring together a fluorescer-quencher pair, as discussed above, leading to a decrease in a fluorescence signal when the analyte sequence is present.

In the above OLA ligation method, the concentration of a target region from an analyte polynucleotide can be increased, if necessary, by amplification with repeated hybridization and ligation steps. Simple additive amplification can be achieved using the analyte polynucleotide as a target and repeating denaturation, annealing, and ligation steps until a desired concentration of the ligated product is achieved.

Alternatively, the ligated product formed by hybridization and ligation can be amplified by ligase chain reaction (LCR), according to published methods (Winn-Deen). In this approach, two sets of sequence-specific oligos are employed for each target region of a double-stranded nucleic acid. One probe set includes first and second oligonucleotides designed for sequence-specific binding to adjacent, contiguous regions of a target sequence in a first strand in the target. The second pair of oligonucleotides are effective to bind (hybridize) to adjacent, contiguous regions of the target sequence on the opposite strand in the target. With continued cycles of denaturation, reannealing and ligation in the presence of the two complementary oligo sets, the target sequence is amplified exponentially, allowing small amounts of target to be detected and/or amplified.

In a further modification, the oligos for OLA or LCR assay bind to adjacent regions in a target polynucleotide which are separated by one or more intervening bases, and ligation is effected by reaction with (i) a DNA polymerase, to fill in the intervening single stranded region with complementary nucleotides, and (ii) a ligase enzyme to covalently link the resultant bound oligonucleotides (Segev, 1992, 1994).

In another embodiment, the target sequences can be detected on the basis of a hybridization-fluorescence assay (Lee et al., 1993). The detection reagents include a sequence-selective binding polymer (FQ-oligo) containing a fluorescer-quencher pair, as discussed above, in which the fluorescence emission of the fluorescer dye is substantially quenched by the quencher when the FQ-oligo is free in solution (i.e., not hybridized to a complementary sequence).

Hybridization of the FQ-oligo to a complementary sequence in the target to form a double-stranded complex is effective to perturb (e.g., increase) the fluorescence signal of the fluorescer, indicating that the target is present in the sample. In another embodiment, the binding polymer contains only a fluorescer dye (but not a quencher dye) whose fluorescence signal either decreases or increases upon hybridization to the target, to produce a detectable signal.

It will be appreciated that since the selected analytes in the sample will usually be tested for under generally uniform temperature and pressure conditions within the device, the detection reagents in the various detection chambers should have substantially the same reaction kinetics. This can generally be accomplished using oligonucleotides and primers having similar or identical melting curves, which can be determined by empirical or experimental methods as are known in the art.

In another embodiment, the analyte is an antigen, and the analyte-specific reagents in each detection chamber include an antibody specific for a selected analyte-antigen. Detection may be by fluorescence detection, agglutination, or other homogeneous assay format. As used herein, "antibody" is intended to refer to a monoclonal or polyclonal antibody, an Fc portion of an antibody, or any other kind of binding partner having an equivalent function.

For fluorescence detection, the antibody may be labeled with a fluorescer compound such that specific binding of the antibody to the analyte is effective to produce a detectable increase or decrease in the compound's fluorescence, to produce a detectable signal (non-competitive format). In an alternative embodiment (competitive format), the detection means includes (i) an unlabeled, analyte-specific antibody, and (ii) a fluorescer-labeled ligand which is effective to compete with the analyte for specifically binding to the antibody. Binding of the ligand to the antibody is effective to increase or decrease the fluorescence signal of the attached fluorescer. Accordingly, the measured signal will depend on the amount of ligand that is displaced by analyte from the sample. Exemplary fluorescence assay formats which may be adapted for the present invention can be found in Ullman (1979, 1981) and Yoshida (1980), for example.

In a related embodiment, when the analyte is an antibody, the analyte-specific detection reagents include an antigen for reacting with a selected analyte antibody which may be present in the sample. The reagents may be adapted for a competitive or non-competitive type format, analogous to the formats discussed above. Alternatively, the analyte-specific reagents include a mono- or polyvalent antigen having one or more copies of an epitope which is specifically bound by the antibody-analyte, to promote an agglutination reaction which provides the detection signal.

In yet another embodiment, the selected analytes are enzymes, and the detection reagents include enzyme-substrate molecules which are designed to react with specific analyte enzymes in the sample, based on the substrate specificities of the enzymes. Accordingly, detection chambers in the device each contain a different substrate or substrate combination, for which the analyte enzyme(s) may be specific. This embodiment is useful for detecting or measuring one or more enzymes which may be present in the sample, or for probing the substrate specificity of a selected enzyme. Particularly preferred detection reagents include chromogenic substrates such as NAD/NADH, FAD/FADH, and various other reducing dyes, for example, useful for assaying hydrogenases, oxidases, and enzymes that generate products which can be assayed by hydrogenases and oxidases. For esterase or hydrolase (e.g., glycosidase) detection, chromogenic moieties such as nitrophenol may be used, for example.

In another embodiment, the analytes are drug candidates, and the detection reagents include a suitable drug target or an equivalent thereof, to test for binding of the drug candidate to the target. It will be appreciated that this concept can be generalized to encompass screening for substances that interact with or bind to one or more selected target substances. For example, the assay device can be used to test for agonists or antagonists of a selected receptor protein, such as the acetylcholine receptor. In a further embodiment, the assay device can be used to screen for substrates, activators, or inhibitors of one or more selected enzymes. The assay may also be adapted to measure dose-response curves for analytes binding to selected targets.

The sample or detection reagents may also include a carrier protein, such as bovine serum albumin (BSA) to reduce non-specific binding of assay components to the walls of the detection chambers.

The analyte-specific detection reagents are preferably dispensed into the detection chambers robotically using a dispensing system designed to deliver small volumes of liquid solutions (e.g., 0.1 to 1 μL). The system is supplied with separate analyte-specific detection reagents which are dispensed to pre-selected detection chambers without cross-contamination.

A reagent loading device that has been prepared in accordance with the invention includes a dispensing robot (Asymtek Automove 402) coupled to a plurality of drop-on-demand ink-jet printing heads. The robot includes an X,Y-axis work table (12 inch×12 inch) having a lateral resolution of 0.001 inch, a lateral velocity of 0-20 inch/sec, a Z-axis resolution of 0.001 inch, and a Z-axis velocity of 0-8 inch/sec. The robot optionally includes a tip locator, offset camera, strobe drop camera, on-axis camera, and/or gravimetric drop calibration. The printing heads are of a drop-on-demand, piezo-electric type, having wetted surfaces usually selected from glass, Teflon?, and polypropylene. The minimum drop volume is 25 mL, and the maximum flow is 1 μL/min.

Reagent loading is preferably accomplished under carefully-controlled sterile conditions using one or more dedicated dispensing robots. After application, the reagents are allowed to dry in the chambers until most or all of the solvent has evaporated. Drying may be accelerated by baking or reduced pressure as appropriate. The detection chambers are then sealed by bonding the chamber containing substrate layer with an appropriate cover layer, and the device is ready for use.

Signal Detection and Analysis

The signal produced by reaction of the analyte-specific reagents with the sample is measured by any suitable detection means, including optical and non-optical methods.

Where the signal is detected optically, detection may be accomplished using any optical detector that is compatible with the spectroscopic properties of the signal. The assay may involve an increase in an optical signal or a decrease. The optical signal may be based on any of a variety of optical principals, including fluorescence, chemiluminescence, light absorbance, circular dichroism, optical rotation, Raman scattering, radioactivity, and light scattering. Preferably, the optical signal is based on fluorescence, chemiluminescence, or light absorbance.

In general, the optical signal to be detected will involve absorbance or emission of light having a wavelength between about 180 nm (ultraviolet) and about 50 μm (far infrared). More typically, the wavelength is between about 200 nm (ultraviolet) and about 800 nm (near infrared). A variety of detection apparatus for measuring light having such wavelengths are well known in the art, and will typically involve the use of light filters, photomultipliers, diode-based detectors, and/or charge-coupled detectors (CCD), for example.

The optical signals produced in the individual detection chambers may be measured sequentially by iteratively scanning the chambers one at a time or in small groups, or may be measured simultaneously using a detector which interrogates all of the detection chambers continuously or at short time intervals. Preferably, the signals are recorded with the aid of a computer capable of displaying instantaneously (in real-time) the signal level in each of the detection chambers, and also storing the time courses of the signals for later analysis.

The optical signal in each chamber may be based on detection of light having one or more selected wavelengths with defined band-widths (e.g., 500 nm±5 nm). Alternatively, the optical signal may be based on the shape or profile of emitted or absorbed light in a selected wavelength range. Preferably, the optical signal will involve measurement of light having at least two distinctive wavelengths in order to include an internal control. For example, a first wavelength is used to measure the analyte, and a second wavelength is used to verify that the chamber is not empty or to verify that a selected reagent or calibration standard is present in the detection chamber. An aberration or absence of the signal for the second wavelength is an indication that the chamber may be empty, that the sample was improperly prepared, or that the detection reagents are defective.

In studies conducted in support of the invention, a detection assembly was prepared for fluorescence detection of target polynucleotides in a sample using a device in accordance with the invention. The assembly includes a translation stage for positioning the test device. The test device includes a 7×7 array of addressable detection chambers containing fluorescent detection reagents. The detector in the assembly consists of a tungsten bulb (or quartz halogen bulb, 75 W) illumination source, a CCD camera, and appropriate focusing/collection optics. The illumination source is positioned so as to illuminate the device diagonally from above (e.g., at an inclination angle of 45 degrees with respect to the illuminated surface). The optics include two lenses separated by an emission filter. The first lens collimates the incoming image for the emission filter, and the second lens which re-images the filtered beam onto the CCD. The test device is placed at the focal point of the first lens.

The CCD is a thermoelectrically cooled, instrumentation-grade front-illuminated CCD (Princeton Instruments TEA/CCD-512TK/1). The detection plate of the CCD has a 512× 512 array of 27 μm square pixels which covers the entire overhead cross-section of the test device. The camera head is controlled by a controller (Princeton Instruments ST-135) which communicates with a computer (Quadra 650, Apple Computers) for collecting and processing the signal data. The system is capable of on-chip binning of the pixels. For detection chambers having an overhead cross-section of 1 mm×1 mm, bins having a size of 2×2 pixels are suitable. More generally, the bin size is selected on the basis of the total processing time that will be required, the sizes and number of detection chambers, sensitivity, and signal noise.

The computer in the assembly includes signal-processing software for selecting an appropriate sub-region in each detection chamber from which the signal is measured. Such sub-regions are selected for uniformity of incoming light, to ensure that edge regions are excluded. The signal image of the device is recorded and stored at selected intervals, according to the requirements of the assay. Preferably, the signal for each detection chamber is recorded as an average signal per bin for the selected sub-region in each chamber, since the size of the selected sub-region in each chamber will usually differ from chamber to chamber.

The detector optics may further be adapted to include a filter wheel for detecting fluorescence at 2 or more wavelengths.

As discussed above, the temperature of the detection chambers may be controlled, if appropriate, by any of a number of suitable methods. In the detection assembly that was prepared in accordance with the invention, the heating means is external to the test device (off-chip heating), and includes a temperature controller (Marlow Industries model SE 5020) equipped with a peltier device (ITI Ferro Tec model 6300) having a ramp rate of about ±4 E/sec in the range of 55 EC to 95 EC. For on-chip heating, where the device includes resistive tracings (or a comparable equivalent) for heating the chambers, the assembly can be modified to provide one or two zones of resistance heating capable of establishing a maximum power dissipation of 25 W over a 200 mm² area; this mode can provide a ramp rate of ±10 E/sec during transition from 55 EC to 95 EC.

The above described structure (Section IIB) for detecting an analyte-related signal in each chamber, including the optical window associated with that chamber, is also referred to herein collectively as detection means for detecting such signal.

Another type of detection means is a biosensor device capable of detecting the reaction of an analyte with an analyte-specific reagent in each chamber. Amperometric biosensors suitable for use in the invention operate on a variety of principles. In one, the analyte being measured is itself capable of interacting with an analyte-specific reagent to generate an electrochemical species, i.e., a species capable of function as an electron donor or acceptor when in contact with an electrode. As an example, reaction of the analyte cholesterol with the reagent cholesterol oxidase generates the electrochemical species $H_2O_2$ which, in contact with an electrode, produces a measurable current in a circuit containing the electrode.

The analyte-specific reagent may be localized on a film separated from the electrode surface by a permselective layer that is selectively permeable to the electrochemical species (and other small components in the sample). When sample fluid is added to the biosensor, reaction of the analyte with the corresponding reagent produces an electrochemical species whose presence and amount are quantitated by current measurement through the electrode.

Alternatively, the analyte-specific reagent may be a receptor which is specific for the analyte. Initially, the receptor sites are filled with an analyte-enzyme conjugate. In the presence of analyte, the conjugates are displaced from the receptor, and are then free to migrate to positions close to the electrode, for production of transient electrochemical species (such as $H_2O_2$ in the presence of catalase) in the vicinity of the electrode.

Another general type of biosensor employs a lipid bilayer membrane as a gate for electrochemical species interposed between a sample-fluid chamber and an electrode. The bilayer is provided with ion-channel proteins which function as ion gates that can be opened by analyte binding to the proteins. Thus, binding of analyte to the channel proteins (which serve as the analyte-specific reagent) leads to ion flow across the membrane and detectable signal at the electrode.

Thin-film biosensors of the type mentioned above may be formed in a microchip or small-substrate format by photolithographic methods, such as described in U.S. Pat. Nos. 5,391,250, 5,212050, 5,200,051, and 4,975,175. As applied to the present invention, the chamber walls in the substrate may serve as the substrate for deposition of the required electrode and film layers. In addition to these layers, suitable conductive connectors connecting the electrodes to electrical leads are also laid down.

In a typical device, each chamber contains a biosensor for a given analyte. When sample is introduced into the device, the multiple sample analytes are then separately measured in the chambers, with the results being reported to a processing unit to which the device is electrically connected.

Assay Method

In another aspect, the invention includes a method for detecting or quantitating a plurality of analytes in a liquid sample. In the method, there is provided a device of the type described above, wherein the interior of the network is placed under vacuum. A liquid sample is then applied to the inlet, and the sample is allowed to be drawn into the sample-distribution network by vacuum action, delivering sample to the detection chambers. The delivered sample is allowed to react with the analyte-specific reagent in each detection chamber under conditions effective to produce a detectable signal when the selected analyte is present in the sample. The reaction chambers are inspected or analyzed to determine the presence and/or amount of the selected analytes in the sample.

The sample tested may be from any source which can be dissolved or extracted into a liquid that is compatible with the device, and which may potentially contain one or more of the analytes of interest. For example, the sample may be a biological fluid such as blood, serum, plasma, urine, sweat, tear fluid, semen, saliva, cerebral spinal fluid, or a purified or modified derivative thereof. The sample may also be obtained from a plant, animal tissue, cellular lysate, cell culture, microbial sample, or soil sample, for example. The sample may be purified or pre-treated if necessary before testing, to remove substances that might otherwise interfere with analyte detection. Typically, the sample fluid will be an aqueous solution, particularly for polar analytes such as polypeptides, polynucleotides, and salts, for example. The solution may include surfactants or detergents to improve analytes solubility. For non-polar and hydrophobic analytes, organic solvents may be more suitable.

As discussed above, the device may be manufactured and sold in a form wherein the sample-distribution network is under vacuum, so that the device is ready to load by the end-user. Alternatively, evacuation of the network is conducted by the user, through a vacuum port or via the sample inlet itself.

Prior to sample loading, any gas in the network may be replaced with another gas, according to the requirements of the assay. In a preferred embodiment, the residual gas is replaced with carbon dioxide, so that any gas bubbles that appear in the network after sample loading are quickly dissolved by the sample fluid, particularly if the sample is an aqueous solution.

It will be appreciated that when the device includes a vacuum port downstream of the detection chambers, the sample delivery channels in the device may be cleared of sample after the detection chambers have been filled, to further isolate the detection chambers from each other. The invention also contemplates filling the delivery channels with an additional fluid, such as a mineral oil or a viscous polymer solution containing agarose or other viscous material (e.g., see Dubrow, U.S. Pat. No. 5,164,055, and Menchen et al., U.S. Pat. No. 5,290,418), to segregate the chambers from each other, or with a reagent-containing solution which facilitates the assay.

In a particularly advantageous embodiment of the invention, a large-volume syringe can be used to generate a vacuum inside the sample distribution network of the device prior to loading. By "large-volume" is meant that the volume of the syringe is greater than the total internal volume of the device (i.e., of the sample distribution network). Preferably, the volume of the syringe is at least 20-fold greater than the interior volume of the device. With reference to the device in FIG. 9, the inlet-tip of the syringe is connected to vacuum port 212. When opening 216 is aligned with opening 179, the syringe is used to draw air from the interior of the device, thereby lowering the internal pressure. For example, if a syringe with a volume of 50 mL is used, and the internal volume of the device is 100 µL, the pressure in the sample distribution network can be reduced by a factor of 500 (=0.1 mL/50 mL). Thus, an initial internal pressure of 760 torr can be reduced to less than 2 torr. With reference to the device in FIG. 6A, the syringe can be connected to fitting 106 or 102 using appropriate connections, to withdraw air from the distribution network.

Accordingly, the present invention includes a kit comprising (i) a device as described above and (ii) a syringe for drawing air from the interior of the device. The invention also includes a method of using the kit to detect one or more analytes in a sample, as described above. It will be appreciated that using a syringe greatly simplifies the step of creating a vacuum inside the device, so that the device can be used quickly or immediately without needing a mechanical vacuum pump.

Utility

The present invention can be used in a wide variety of applications. The invention can be used for medical or veterinary purposes, such as detecting pathogens, diagnosing or monitoring disease, genetic screening, determining antibody or antigen titers, detecting and monitoring changes in health, and monitoring drug therapy. The invention is also useful in a wide variety of forensic, environmental, and industrial applications, including screening drug candidates for activity.

More generally, the present invention provides a convenient method for simultaneous assay of multiple analytes in a sample. The invention is highly flexible in its applications, being adaptable to analysis of a wide variety of analytes and sample materials. By providing pre-dispensed, analyte-specific reagents in separate detection chambers, the invention eliminates the need for complicated and time-consuming reagent preparation.

Practice of the invention is further simplified since the detection chambers can be loaded via a single sample inlet. The use of uniformly sized detection chambers renders the device self-metering, in that a precise volume of sample is delivered to each chamber. Thus, the precision, accuracy, and reproducibility of the assay are all enhanced, since the quantities and compositions of the analyte-specific reagents, the quantity of sample in the chambers, and the reaction conditions can be carefully controlled. Moreover, very small volumes of sample are required since the dimensions of the sample-distribution network in the device can be very small.

The device may be formed from a wide variety of materials, allowing the composition of the device to be adapted to the particular reagents and conditions in the assay. Inasmuch as the device requires no moving parts, and can be relatively small in size (typically having dimension on the order of millimeters to centimeters), manufacture of the device is simplified and costs are reduced.

The features and advantages of the invention may be further understood from the following example, which is not intended in any way to limit the scope of the invention.

EXAMPLE

The following study was performed using a polycarbonate microdevice substantially as shown in FIG. 9, to demonstrate detection of a human β-actin gene by PCR (polymerase chain reaction). The assay components for PCR detection were obtained from PE Applied Biosystems (Foster City, Calif., β-actin kit, part #N808-0230). The kit components included the following stock solutions:

β-actin forward primer:
3 µM primer in 10 mM Tris-HCl, pH 8.0 (at room temperature), 1 mM EDTA β-actin reverse primer:
3 µM primer in 10 mM Tris-HCl, pH 8.0 (at room temperature), 1 mM EDTA β-actin probe:
2 µM TAMRA-labeled probe in 10 mM Tris-HCl, pH 8.0 (at room temperature), 1 mM EDTA DNA sample:
370 µg/mL human genomic DNA in 10 mM Tris-HCl, pH 8.0 (at room temperature), 1 mM EDTA (from Coriell Cell Repositories, Camden, N.J.)

dNTPs:
20 mM dNTP (1 tube each for dUTP, dATP, dCTP and dGTP) in autoclaved deionized ultrafiltered water, titrated to pH 7.0 with NaOH DNA polymerase:
"AMPLITAQ GOLD" DNA polymerase at 5 U/µL, from PE Applied Biosystems, part # N808-0240 (PE Applied Biosystems "AMPLITAQ GOLD" Product Brochure, 1996)

"AMPERASE" UNG:
uracil-N-glycosylase at 1 U/µL, from PE Applied Biosystems, part #N808-0096

10× "TAQMAN" buffer A:
500 mM KCl, 100 mM Tris-HCl, 0.1 M EDTA, 600 nM Passive Reference 1 (ROX), pH 8.3 at room temperature, autoclaved $MgCl_2$:
20 mM $MgCl_2$ in autoclaved deionized ultrafiltered water A description of the sequences of the forward primer, the reverse primer, and the TAMRA-labeled probe can be found in PE Applied Biosystems "TAQMAN" PCR Reagent Protocol (1996), which also describes the general steps of the "TAQMAN" assay technique. The forward and reverse primers were effective to produce a 297 basepair PCR product.

A flat substrate layer 180 and a substrate layer 161 were formed from polycarbonate by standard injection-molding methods (substrate layer 161) or from sheet stock (layer 180). The volume of each detection chamber was 1 µL.

Detection chambers were loaded with different amounts of forward primer, reverse primer, and fluorescent probe as follows. To a polypropylene tube was added 0.5 mL each of β-actin forward primer solution, reverse primer solution, and fluorescent probe, to give a final primer/probe stock solution volume of 1.5 mL. This solution was then loaded into alternating detection chambers in substrate layer 161 using a robotically controlled microsyringe. Specifically, alternate chambers were loaded with either a 1×, 5× or 10× amount of primer/probe solution, with 1× (14 mL primer/probe stock solution) being equivalent to a final concentration in a detection chamber of 15 nM of each primer and 10 nM of fluorescent probe (after the dried chamber is subsequently filled with sample), 5× (72 mL primer/probe stock solution) being equivalent to a final concentration of 75 nM of each primer and 50 nM of fluorescent probe, and 10× (145 mL primer/probe stock solution) being equivalent to a final concentration of 150 nM of each primer and 100 nM of fluorescent probe. The amounts of primer and probe in the loaded chambers corresponded to 1/20, 1/4, and 1/2 of the concentrations used under standard reaction conditions, for the 1×, 5×, and 10× chambers, respectively. The loaded chambers produced a "checkerboard" pattern in substrate layer 161 where each loaded chamber was separated by an intervening empty chamber.

After the loaded chambers were allowed to air-dry to dryness at room temperature, the loaded substrate layer (161)

was joined to a flat substrate layer 180 by ultrasonic welding. Inlet fitting 190 was then placed over sample inlet 162, such that opening 179 was aligned with vacuum port opening 216. The sample distribution network 164 and detection chambers 168 were evacuated via vacuum port 212, which was connected to a vacuum pump, to a final internal pressure of approximately 1 to 10 torr.

The PCR reaction mixture (sample), without primers and probe, was prepared from the above stock solutions to give the following final concentrations in the sample:

10 mM Tris-HCl, pH 8.3
50 mM KCl
3.5 mM $MgCl_2$
400 μM dUTP
200 μM each dATP, dCTP, and dGTP
U/μL uracil-N-glycosylase
0.25 U/μL "AMPLITAQ GOLD" DNA polymerase
0.74 ng/μL human genomic DNA template For loading of sample into the microdevice, a micropipette loaded with the above sample solution was placed in sample port 214 so as to minimize the deadvolume occupied by air at the tip of the pipette. Inlet fitting 190 was then pressed down further to align opening 179 with opening 218, so that the sample was drawn from port 214 into the detection chambers by vacuum action. Filling of the chambers was complete in less than a second.

The microdevice was then clamped to a peltier device (20 mm×20 mm) glued to an aluminum heat sink. Cycling was controlled using a Marlow temperature controller (Marlow Industries Inc., Dallas, Tex., Model No. SE 5020). A thermistor was attached to the peltier device to provide temperature feedback (Marlow part No. 217-2228-006). The microdevice was thermocycled as follows:

precycle: 50 EC for 2 minutes; 95 EC for 10 minutes;
40 cycles: 95 EC for 15 seconds, 60 EC for 1 minute;
hold at 72 EC.

Signal detection was accomplished using a fluorescence detection instrument consisting of a tungsten bulb for illumination and a CCD camera and 4-color filter wheel for detection. Images of all detection chambers (wells) were taken at the end of each thermocycle (during the 60 EC step) at several wavelengths in order to monitor the increase of the reporter's fluorescence. Interfering fluorescence fluctuations were normalized by dividing the emission intensity of the reporter dye by the emission intensity of the passive reference (ROX dye) for a given chamber. The excitation wavelength was 488 nm. The reporter intensity was measured at 518 nm, and the passive reference intensity was measured at 602 nm.

Results

Positive fluorescent signals were detected in all chambers that had been loaded with the β-actin primers and fluorescent probe at the 5× and 10 concentrations. Little or no signal was detected for chambers loaded at the 1× concentration. No detectable signal was detected above background for the chambers which did not contain β-actin primer and probe, indicating that there was no cross-contamination between detection chambers after 40 heat/cool cycles.

The highest final fluorescence signals were obtained in detection chambers loaded with a 10× amount of primers and probe, with detectable signals appearing after about 23 cycles. The 5× chambers also showed detectable signals after cycle 23, but the final fluorescence signal was not as high as that for the 10× wells (due to lower probe concentration). Thus, the β-actin gene was readily detected using primer and probe concentrations equal to ¼ and ½ of those used under ordinary conditions. The results also show that the preloaded primers and probes were successfully dissolved in the sample after sample loading.

Although the invention has been described by way of illustration and example for purposes of clarity and understanding, it will be appreciated that various modifications can be made without departing from the invention. All references cited above are incorporated herein by reference.

What is claimed is:

1. A method for reacting a target nucleic acid and detecting an optical signal, comprising:
   providing a substrate comprising a chamber, wherein the chamber is pre-loaded with a first unlabeled oligonucleotide such that the first unlabeled oligonucleotide is immobilized on the substrate, and the chamber is pre-loaded with a second unlabeled oligonucleotide such that the second unlabeled oligonucleotide is immobilized on the substrate;
   introducing a target nucleic acid sequence into the chamber;
   reacting the target nucleic acid sequence with both the first unlabeled oligonucleotide and the second unlabeled oligonucleotide in the chamber, to form a first reaction product in the chamber;
   reacting the first reaction product with an optically detectable detection reagent in the chamber to form a second reaction product; and
   detecting an optical signal produced in the chamber by the second reaction product in the chamber,
   wherein the substrate further comprises a channel in fluid communication with the chamber.

2. The method of claim 1, wherein reacting the target nucleic acid sequence with both the first unlabeled oligonucleotide and the second unlabeled oligonucleotide in the chamber, to form a first reaction product in the chamber, comprises at least one of a polymerase chain reaction, a ligase chain reaction, an oligonucleotide ligation assay, and a hybridization assay.

3. The method of claim 1, wherein the first unlabeled oligonucleotide and the second unlabeled oligonucleotide comprise a primer pair suitable for amplifying the target nucleic acid sequence.

4. The method of claim 1, wherein at least one of the first unlabeled oligonucleotide and the second unlabeled oligonucleotide comprises a sequence that is complementary to at least a portion of the target nucleic acid sequence.

5. The method of claim 1, wherein the second reaction product is detected through an optically transparent window in the chamber.

6. The method of claim 1, wherein the target nucleic acid sequence is introduced into the chamber by vacuum action.

7. The method of claim 1, wherein at least one of the pre-loaded first unlabelled oligonucleotide and the pre-loaded second unlabelled oligonucleotide are dried in the chamber.

8. The method of claim 1, wherein the optically detectable detection reagent comprises a fluorescent dye.

9. The method of claim 1, wherein the optically detectable detection reagent comprises a fluorescer dye and a quencher dye.

10. The method of claim 1, wherein at least one of the first unlabeled oligonucleotide and the second unlabeled oligonucleotide comprises a polynucleotide analog.

11. The method of claim 1, wherein the first unlabeled oligonucleotide and the second unlabeled oligonucleotide bind to adjacent, contiguous regions of the target nucleic acid sequence.

12. The method of claim 1, wherein the first unlabeled oligonucleotide has a sequence that is complementary to at least a portion of the target nucleic acid sequence.

13. The method of claim 1, wherein the second unlabeled oligonucleotide has a sequence that is complementary to at least a portion of the target nucleic acid sequence.

14. The method of claim 1, wherein the first unlabeled oligonucleotide has a sequence that is complementary to at least a first portion of the target nucleic acid sequence, and where the second unlabeled oligonucleotide has a sequence that is complementary to at least a second portion of the target nucleic acid sequence.

15. The method of claim 1, wherein the reacting of the target nucleic acid sequence with both the first unlabeled oligonucleotide and the second unlabeled oligonucleotide in the chamber, further comprises reacting the target nucleic acid sequence with nucleotide triphosphates, to form the first reaction product in the chamber.

16. The method of claim 1, wherein the chamber comprises a plurality of chambers formed in the substrate, the channel comprises a plurality of channels, and each of the plurality of chambers is in fluid communication with one of the plurality of channels.

* * * * *

UNITED STATES PATENT AND TRADEMARK OFFICE
CERTIFICATE OF CORRECTION

| | |
|---|---|
| PATENT NO. | : 8,247,219 B2 |
| APPLICATION NO. | : 11/811504 |
| DATED | : August 21, 2012 |
| INVENTOR(S) | : Woudenberg et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 552 days.

Signed and Sealed this
Seventeenth Day of March, 2020

Andrei Iancu
*Director of the United States Patent and Trademark Office*